US011279762B2

(12) United States Patent
Hongo et al.

(10) Patent No.: US 11,279,762 B2
(45) Date of Patent: Mar. 22, 2022

(54) IDIOTYPIC ANTIBODIES AGAINST ANTI-PD-L1 ANTIBODIES AND USES THEREOF

(71) Applicant: Genentech, Inc., South San Francisco, CA (US)

(72) Inventors: Jo-Anne Hongo, South San Francisco, CA (US); Angie Yee, South San Francisco, CA (US); Christine Tan, South San Francisco, CA (US); Joyce Lai, South San Francisco, CA (US); Joanne Adamkewicz, South San Francisco, CA (US); John Byon, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 302 days.

(21) Appl. No.: 16/511,323

(22) Filed: Jul. 15, 2019

(65) Prior Publication Data

US 2019/0338034 A1    Nov. 7, 2019

Related U.S. Application Data

(63) Continuation of application No. PCT/US2018/014099, filed on Jan. 17, 2018.

(60) Provisional application No. 62/447,886, filed on Jan. 18, 2017, provisional application No. 62/452,934, filed on Jan. 31, 2017.

(51) Int. Cl.
  *C07K 16/28* (2006.01)
  *C12P 21/00* (2006.01)
  *G01N 33/68* (2006.01)

(52) U.S. Cl.
  CPC ........ *C07K 16/2827* (2013.01); *C12P 21/005* (2013.01); *G01N 33/68* (2013.01); *G01N 33/686* (2013.01); *C07K 2317/14* (2013.01); *C07K 2317/24* (2013.01); *C07K 2317/56* (2013.01); *C07K 2317/76* (2013.01); *C07K 2317/92* (2013.01); *G01N 2800/26* (2013.01); *G01N 2800/52* (2013.01)

(58) Field of Classification Search
  CPC ............ C07K 16/2827; C07K 16/4208; C07K 2317/565; C07K 2317/14; C07K 2317/24; C07K 2317/56; C07K 2317/76; C07K 2317/92; G01N 2800/52; G01N 33/686; G01N 2800/26; G01N 33/68; G01N 2333/70532
  See application file for complete search history.

(56) References Cited

U.S. PATENT DOCUMENTS

| | | |
|---|---|---|
| 3,645,852 A | 2/1972 | Axen |
| 3,691,016 A | 9/1972 | Patel |
| 3,940,475 A | 2/1976 | Gross |
| 3,969,287 A | 7/1976 | Jaworek |
| 4,195,128 A | 3/1980 | Gribnau |
| 4,229,537 A | 10/1980 | Hodgins |
| 4,247,642 A | 1/1981 | Hirohara |
| 4,330,440 A | 5/1982 | Ayers |
| 4,376,110 A | 3/1983 | David |
| 3,720,760 A | 2/1984 | Wide |
| 4,737,456 A | 4/1988 | Weng |
| 4,816,567 A | 3/1989 | Cabilly |
| 5,648,237 A | 7/1997 | Carter |
| 5,789,199 A | 8/1998 | Pettit et al. |
| 5,840,523 A | 11/1998 | Simmons et al. |
| 5,959,177 A | 9/1999 | Hein et al. |
| 6,020,208 A | 2/2000 | Hutchens |
| 6,040,498 A | 3/2000 | Stomp et al. |
| 6,417,429 B1 | 7/2002 | Hein et al. |
| 6,420,548 B1 | 7/2002 | Vezina et al. |
| 6,579,719 B1 | 6/2003 | Hutchens |
| 6,811,689 B2 | 11/2004 | Zhang |
| 7,125,978 B1 | 10/2006 | Vezina et al. |
| 8,217,149 B2 | 7/2012 | Irving |

FOREIGN PATENT DOCUMENTS

| | | |
|---|---|---|
| CN | 102245640 A | 11/2011 |
| CN | 104334583 A | 2/2015 |
| CN | 105209919 A | 12/2015 |
| CN | 105492025 A | 4/2016 |
| CN | 105899535 A | 8/2016 |
| CN | 106103482 A | 11/2016 |
| WO | WO199209690 A2 | 6/1992 |
| WO | WO199209690 A3 | 12/1992 |
| WO | 2010077634 A1 | 7/2010 |
| WO | WO2013148373 A1 | 10/2013 |
| WO | 2014151006 A2 | 9/2014 |
| WO | 2014151006 A3 | 11/2014 |
| WO | 2015009856 A2 | 1/2015 |
| WO | 2015009856 A3 | 4/2015 |
| WO | 2015095410 A1 | 6/2015 |
| WO | 2015112805 A1 | 7/2015 |
| WO | WO2016183326 A1 | 11/2016 |
| WO | 2016205566 A1 | 12/2016 |

(Continued)

OTHER PUBLICATIONS

Miguel Blood 2002 99:1853-1856 (Year: 2002).*
Paiva Leukemai 2015 29: 2110-2113 (Year: 2015).*
Almagro, J.C. et al. (Jan. 1, 2008). "Humanization of Antibodies," Frontiers in Bioscience 13:1619-1633.
Bass, S. et al. (1990). "Hormone Phage: An Enrichment Method for Variant Proteins With Altered Binding Properties," Proteins 8:309-314.
Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.
Charlton, K.A. (2003), "Chapter 14: Expression and Isolation of Recombinant Antibody Fragments in *E. coli*," in Methods in Molecular Biology Lo, B.K.C. ed., Humana Press: Totowa, NJ, pp. 245-254.

(Continued)

*Primary Examiner* — Changhwa J Cheu
(74) *Attorney, Agent, or Firm* — Morrison & Foerster LLP

(57) ABSTRACT

The invention provides anti-idiotypic antibodies against anti-PD-L1 antibodies and methods of using the same.

29 Claims, 8 Drawing Sheets

Specification includes a Sequence Listing.

(56) References Cited

FOREIGN PATENT DOCUMENTS

| WO | WO2016205551 A2 | 12/2016 |
|---|---|---|
| WO | WO2016205551 A3 | 2/2017 |

OTHER PUBLICATIONS

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Chothia, C. et al. (1987). "Canonical Structures for the Hypervariabie Regions of Immunoglobulins," J. Mol. Biol. 196:901-917.

Chowdhury et al. (2008) "Engineering Hot Spots For Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Cunningham, B.C. et al. (Jun. 2, 1989). "High-Resolution Epitope Mapping of hGH-Receptor Interactions by Alanine-Scanning Mutagenesis," Science 244:1081-1085.

David, G.S. et al. (1974). "Protein Iodination With Solid State Lactoperoxidase," Biochemistry 13(5):1014-1021.

Flatman, S. et al. (2007, e-pub, Dec. 11, 2006), "Process Analytics for Purification of Monoclonal Antibodies," J. Chromatogr. B. 848:79-87.

Gale, D.C. et al. (1993). "Small Volume and Low Flow-Rate Electrospray Ionization Mass Spectrometry of Aqueous Samples," Rapid Commun. Mass Spectrom. 7:1017-1021.

Gerngross, T.U. (Nov. 2004). "Advances in the Production of Human Therapeutic Proteins in Yeasts and Filamentous Fungi," Nat. Biotech. 22(11):1409-1414.

Goding, J.W. (1986). Monoclonal Antibodies: Principles and Practice, pp. 59-103.

Graham, T.L. et al. (1977). "Characteristics of a Human Cell Line Transformed by DNA From Human Adenovirus Type 5," J. Gen. Virol. 36:59-72.

Griffiths, A.D. et al. (1993). "Human Anti-Seif Antibodies With High Specificity From Phage Display Libraries," EMBO J. 12(2):725-734.

Hagman, C. et al. (Feb. 15, 2008, e-pub. Jan. 25, 2008). "Absolute Quantification of Monoclonal Antibodies in Biofluids by Liquid Chromatography-Tandem Mass Spectrometry," Anal. Chem. 80(4):1290-1296.

Hoogenboom, H.R. et al. (1992), "By-Passing Immunisation. Human Antibodies From Synthetic Repertoires of Germline VH Gene Segments Rearranged in Vitro," J. Mol. Biol. 227:381-388.

Hoogenboom, H.R. et al. (2001). "Overview of Antibody Phage-Display Technology and Its Applications," Chapter 1 in Methods in Molecular Biology, O'Brien et al., ed., Human Press, Totowa, New Jersey, 178:1-37.

Hunter, W.M. et al. (May 5, 1962). "Preparation Iodine-131 Labelled Human Growth Hormone of High Specific Activiey," Nature 144:495-496.

International Preliminary Report on Patentability dated Jul. 23, 2019, 20, 2018, for PCT Application No. PCT/US2018/014099, filed Jan. 17, 2018, 6 pages.

International Search Report and Written Opinion, dated Mar. 20, 2018, for PCT Application No. PCT/US2018/014099, filed Jan. 17, 2018, 9 pages.

Kabat, E.A, et al. (1991). Sequences of Proteins of Immunological Interest, 5th ed., Public Health Service, National Institutes of Health, Bethesda, MD. TOC, 21 pages.

Kindt, T.J. et al. (2007). "Antigens and Antibodies," Chapter 4 In Kuby Immunology 6th Ed., W.H. Freeman and Co., p. 91.

Kohler, G. et al. (Aug. 7, 1975) "Continuous Cultures of Fused Cells Secreting Antibody of Predefined Specificity," Nature 256:495-497.

Kozbor, D. J. (Dec. 1984), "A Human Hybrid Myeloma For Production of Human Monoclonal Antibodies," Immunol. 133(6):3001-3005.

Körner, R. et al. (Feb. 1996), "Nano Electrospray Combined With a Quadrupole Ion Trap For the Analysis of Peptides and Protein Digests," J. Am. Soc. Mass Spectrom. 7(2):150-156.

Li, H. et al. (Feb. 2006, e-pub. Jan. 22, 2006). "Optimization of Humanized IgGs in Glycoengineered Pichia Pastoris," Nat. Biotech. 24(2):210-215.

Marks, J.D. et al., (1991). "By-Passing Immunization. Human Antibodies From V-Gene Libraries Displayed on Phage," J. Mol. Biol. 222:581-597.

Marks, J.D. et al. (Jul. 1992). "By-Passing Immunization: Building Affinity Human Antibodies by Chain Shuffling," Bio/Technology 10:779-783.

Mather, J.P. (1980). "Establishment and Characterization of Two Distinct Mouse Testicular Epithelial Cell Lines," Biol. Reprod. 23:243-251.

Mather, J.P. et al. (1982). "Culture of Testicular Cells in Hormone-Supplemented Serum-Free Medium," Annals NY Acad. Sci. 383:44-68.

McCafferty, J. et al. (Dec. 6, 1990). "Phage Antibodies: Filamentous Phage Displaying Antibody variable Domains," Nature 348:552-554.

McCudden, C. et al. (2016) "Monitoring Multiple Myeloma Patients Treated With Daratumumab: Teasing Out Monoclonal Antibody Interference," Clin. Chem. Lab Med. 54(6):1095-1104.

McCudden, C. et al. (May 29-Jun. 2, 2015). "Assessing Clinical Response in Multiple Myeloma (MM) Patients Treated With Monoclonal Antibodies (mAbs): Validation of a Daratumumab IFE Reflex Assay (DIRA) to Distingusih Malinant M-Protein From Therapeutic Antibody," Annual Meeting of the American Society for Clinical Onology (ASCO) Poster 8590, 1 page.

McCudden, C.R. et al. (2010). "Interference of Monoclonal Antibody Therapies with Serum Protein Electrophoresis Tests," Clinical Chemistry 56(12): 1897-1904.

Mesmin, C. et al. (Mar. 2011). "MS-Based Approaches for Studying the Pharmacokinetics of Protein Drugs," Bioanalysis 3(5):477-480.

Mesmin, C. et al. (Oct. 15, 2010). "Liquid Chromatography/Tandem Mass Spectrometry Assay for the Absolute Quantification of the Expected Circulating Apelin Peptides in Human Plasma," Rapid Commun. Mass Spectrom. 24(19):2875-2884.

Munson, P.J. et al. (1980). "Ligand: A Versatile Computerized Approach for Characterization of Ligand-Binding Systems," Anal. Biochem. 107:220-239.

Niels, W.C.J. et al. (2016) "Interference of Daratumumab in Monitoring Multiple Myeloma Patients Using Serum Immunofixation Electrophoresis Can Be Abrogated Using the Daratumumab IFE Reflex Assay (DIRA)," Clin. Chem. Lab Med. 54(6):1105-1109.

Nygren, H. (May 1982). "Conjugation of Horseradish Peroxidase to Fab Fragments With Different Homobifunctional and Heterobifunctional Cross-Linking Reagents. A Comparative Study," J. Histochem. and Cytochem. 30(5):407-412.

O'Sullivan, M.J. et al. (1981). "Methods for the Preparation of Enzyme-antibody Conjugates for Use in Enzyme Immunoassay," in Methods in Enzymology 73:147-166.

Pain, D. et al. (1981). "Preparation of Protein A—Peroxidase Monoconjugate Using a Heterobifunctional Reagent, and Its Use in Enzyme Immunoassays," J. Immunol. Methods 40:219-230.

Plückthun, A. (1992). "Mono- and Bivalent Antibody Fragments Produced in *Escherichia coli*: Engineering, Folding and Antigen Binding," Immunol. Revs. 130:151-188.

Portolano, S. et al. (Feb. 1, 1993). "Lack of Promiscuity in Autoantigen-Specific H and L Chain Combinations as Revealed by Human H and L Chain "Roulete"," J. Immunol. 150(3):880-887.

Powles, T. et al. (Nov. 27, 2014). "MPDL3280A (anti-PD-L1) Treatment Leads To Clinical Activity In Metastatic Bladder Cancer," Nature 515(7528):558-562.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Rotmans, J.P. et al. (1983). "Cross-Linking of Schistosoma mansoni Antigens and Their Covalent Binding on the Surface of Polystyrene Microtitration Trays for Using in the ELISA," J. Immunol. Methods 57:87-98.

Singleton, P. et al. (1994). Dictionary of Microbiology and Molecular Biology 2nd ed., J. Wiley & Sons (New York, N.Y.), 8 pages.

(56) References Cited

OTHER PUBLICATIONS

Skerra, A. (1993). "Bacterial Expression of Immunoglobulin Fragments," Curr. Opinion in Immunol. 5:256-262.
Urlaub, G. et al. (Jul. 1980). "Isolation of Chinese hamster cell mutants deficient in dihydrofolate reductase activity," Proc. Natl. Acad. Sci. USA 77(7):4216-4220.
Van De Donk, N.W. et al. (Jun. 1, 2016, e-pub. Jan. 21, 2016). "Interference of Daratumumab in Monitoring Multiple Myeloma Patients Using Serum Immunofixation Electrophoresis Can Be Abrogated Using The Daratumumab IFE Reflex Assay (DIRA)," Clinical Chemistry And Laboratory Medicine 54(6):1105-1109.
Waterhouse, P. et al. (1993). "Combinatorial Infection and in Vivo Recombination: a Strategy for Making Large Phage Antibody Repertoires," Nucl. Acids Res., 21(9):2265-2266.
Wilm, M. et al. (Jan. 1, 1996). "Analytical Properties of the Nanoelectrospray Ion Source," Anal. Chem. 68(1):1-8.
Winter, G. et al. (1994). "Making Antibodies by Phage Display Technology," Ann. Rev. Immunol. 12:433-455.
Yazaki et al. (2003). Methods in Molecular Biology, Lo, B.K.C. ed., Humana Press: Totowa, N.J., 248:255-268.
Chen, C. et al. (2016). "New Insights Into the Anti-PD-L1 and Anti-PD-1 Regents in Cancer Therapy," European Journal of Inflammation 14(1):61-65.
Wei, M.-L. et al. (Apr. 2016). "PD-1-PD-L1 Antibody in Clinical Cancer Therapy," Chinese Bulletin of Life Sciences 28(4):475-479. English Abstract.

* cited by examiner

Anti-PDL1 Anti-ID Heavy Chain Sequences

Heavy chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 105D11 anti-PDL1 anti-ID | E | V | Q | L | V | E | T | G | G | G | L | V | K | P | G | G | S | L | K | L | S | C | A | A | S | G | F | A | F | S | S | Y | D | M | S | W | V | R | Q | T | P | E |
| 43B5 anti-PDL1 anti-ID | E | V | Q | L | Q | Q | S | G | P | E | L | V | K | P | G | A | S | V | K | I | S | C | K | A | S | G | Y | S | F | T | D | Y | I | M | L | W | V | K | Q | S | H | G |
| 48C1 anti-PDL1 anti-ID | E | V | Q | L | V | E | S | G | G | G | L | V | K | P | G | G | S | L | K | L | S | C | A | A | S | G | F | A | F | S | S | Y | D | M | S | W | V | R | Q | T | P | E |

| Kabat number | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|---|---|---|---|---|---|---|---|---|---|---|---|---|---|---|---|---|---|---|---|---|
| 105D11 anti-PDL1 anti-ID | K | R | L | E | W | V | A | Y | I | S | S | G | G | S | T | Y | Y | P | D | T | V | K | G | R | F | T | I | S | R | D | N | A | K | N | T | L | Y | L |
| 43B5 anti-PDL1 anti-ID | K | S | L | E | W | I | G | N | I | N | P | Y | Y | G | S | T | S | Y | N | L | K | F | K | G | K | A | T | L | T | V | D | K | S | S | T | A | Y | M |
| 48C1 anti-PDL1 anti-ID | K | R | L | E | W | V | A | Y | I | S | S | G | G | S | T | Y | Y | P | D | T | V | K | G | R | F | T | I | S | R | D | N | A | K | N | T | L | Y | L |

| Kabat number | 82a | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|
| 105D11 anti-PDL1 anti-ID | S | L | K | S | E | D | T | A | M | Y | Y | C | A | R | L | V | Y | Y | D | D | Y | D | D | A | M | D | Y | W | G | Q | G | T | S | V | T | V | S | S |
| 43B5 anti-PDL1 anti-ID | Q | L | S | L | T | S | E | D | S | A | V | Y | Y | C | A | R | W | G | G | N | Y | E | G | W | F | A | Y | W | G | Q | G | T | L | V | T | V | S | A |
| 48C1 anti-PDL1 anti-ID | Q | L | S | L | K | S | E | D | T | A | M | Y | Y | C | A | R | T | I | Y | Y | G | Y | D | D | V | M | D | Y | W | G | Q | G | T | S | V | T | V | S | S |

FIG. 1

Anti-PDL1 Anti-ID Light Chain Sequences

Light chain variable region

| Kabat number | 1 · · · · · · · · 10 · · · · · · · · · 20 · · · · · · · · · 30 · · · · · · · · · 40 · · |
|---|---|
| 105D11 anti-PDL1 anti-ID | D I V L T Q S P A I M S A S P G E K V T I T C S A S . S S V S Y M H W F Q Q K P G T |
| 43B5 anti-PDL1 anti-ID | D I K M T Q S P S S M S V S L G D T V S I T C H A S Q G I S S N I G W L Q Q K P G K |
| 48C1 anti-PDL1 anti-ID | Q I V L T Q S P A I M S A S P G E K V T I T C S A S . S S V S Y M H W F Q Q K P G T |

CDR L1 – Contact / CDR L1 – Kabat

| Kabat number | · · 50 · · · · · · · · · 60 · · · · · · · · · 70 · · · · · · · · · 80 · · · · · · · |
|---|---|
| 105D11 anti-PDL1 anti-ID | S P K L W I Y S T S N L A S G V P A R F S G S G S G T S Y S L T I S R M E A E D F A |
| 43B5 anti-PDL1 anti-ID | S F K G L I Y H G T N L E D G V P S R F S G S G S G T A D Y S L T I S S L E S E D F A |
| 48C1 anti-PDL1 anti-ID | S P K L W I Y S T S N L A S G V P A R F S G S G S G T S Y S L T I S R M E A E D A A |

CDR L2 – Contact / CDR L2 – Kabat

| Kabat number | · · 90 · · · · · · · · · 100 · · · · · · 107 |
|---|---|
| 105D11 anti-PDL1 anti-ID | T Y Y C Q Q R S S Y P P P T F G G G T K L E I K |
| 43B5 anti-PDL1 anti-ID | D Y Y C V Q Y A Q F P L T F G A G T K L E L K |
| 48C1 anti-PDL1 anti-ID | T Y Y C Q Q R S G Y P P T F G G G T K L E I K |

CDR L3 – Contact / CDR L3 – Kabat

FIG. 2

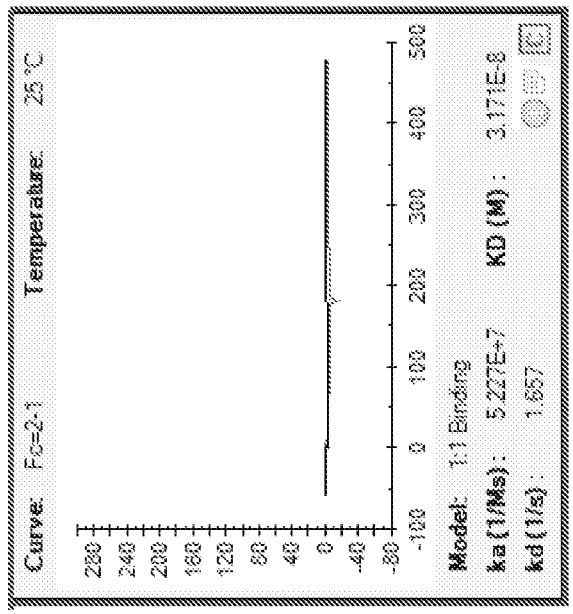
Anti-ID: 105D11
YW167B.43 Negative Control: 500 nM
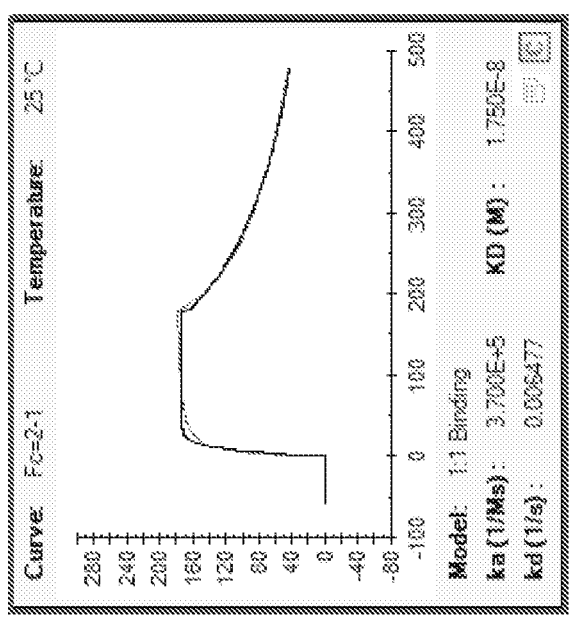
Anti-ID: 105D11
Anti-PDL1 Antibody Fab: 500 nM
FIG. 3

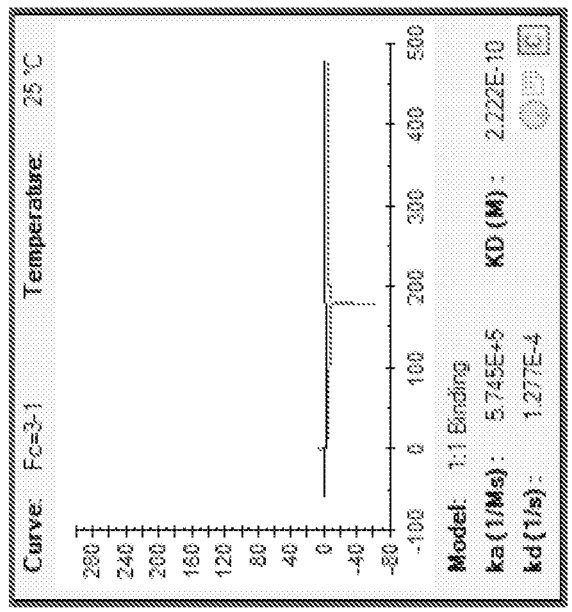
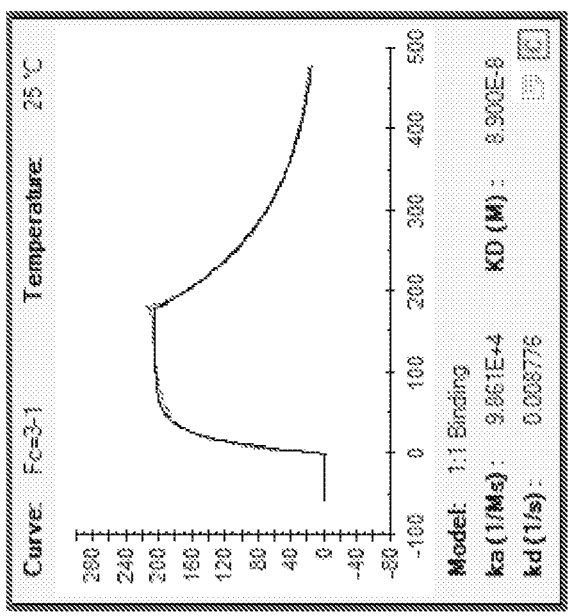
FIG. 4

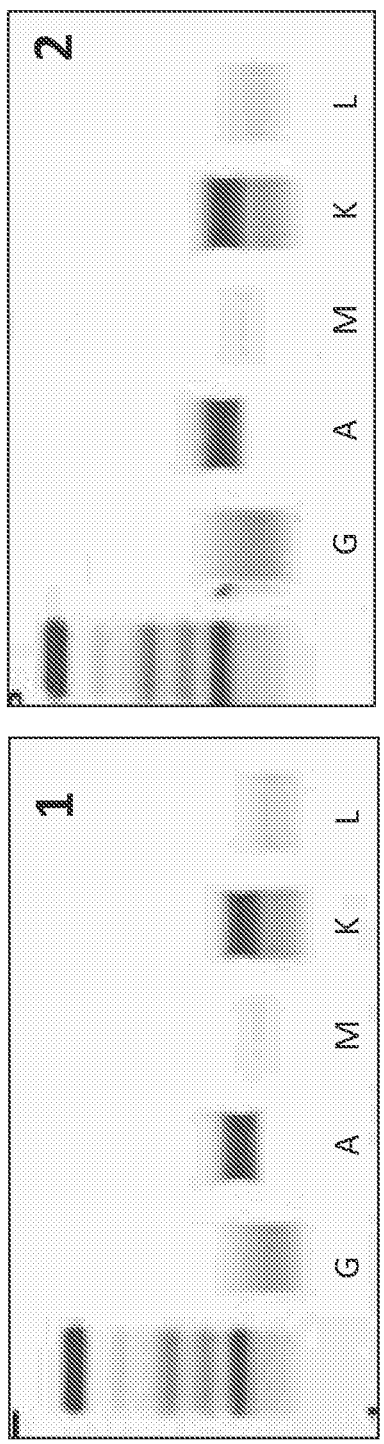
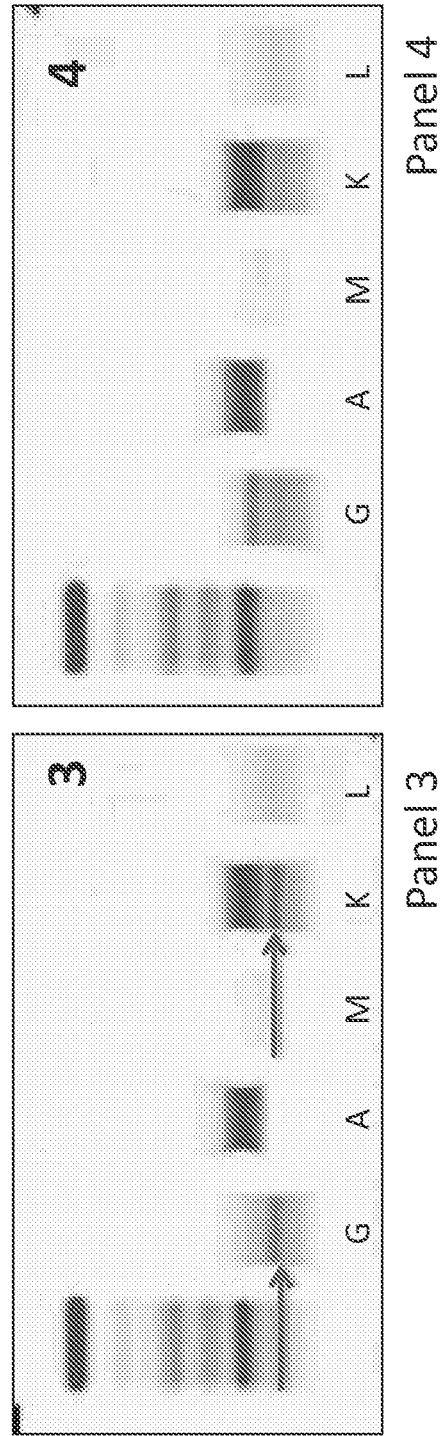
FIG. 7

US 11,279,762 B2

IDIOTYPIC ANTIBODIES AGAINST ANTI-PD-L1 ANTIBODIES AND USES THEREOF

RELATED APPLICATIONS

This application is a continuation of International Application No. PCT/US2018/014099, filed on Jan. 17, 2018, which claims priority benefit to U.S. Patent Application No. 62/447,886, filed Jan. 18, 2017, and U.S. Patent Application No. 62/452,934, filed Jan. 31, 2017, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392038501SEQLIST.TXT, date recorded: Jul. 11, 2019 size: 40 KB).

FIELD OF THE INVENTION

The present invention relates to anti-PD-L1 idiotypic antibodies and methods of using the same.

BACKGROUND OF THE INVENTION

It has been discovered that T cell dysfunction or anergy occurs concurrently with an induced and sustained expression of the inhibitory receptor, programmed death 1 polypeptide (PD-1). As a result, therapeutic targeting PD-1 and other molecules which signal through interactions with PD-1, such as programmed death ligand 1 (PD-L1), are an area of intense interest. The inhibition of PD-L1 signaling has been demonstrated as a means to enhance T cell immunity for the treatment of cancer (e.g., tumor immunity). Therapies which use anti-PD-1 or anti-PD-L1 antibodies have been developed and used for treating different types of cancers. See, e.g., U.S. Pat. No. 8,217,149.

There is a need in the art to detect therapeutic monoclonal antibodies to PD-L1 in biological samples and/or clinical samples without also detecting other antibodies directed or not directed to PD-L1 (e.g., endogenous immunoglobulins). The invention provides anti-idiotypic antibodies that specifically detect certain anti-PD-L1 antibodies. These antibodies are useful, for example, in pharmacokinetic (PK) and pharmacodynamic studies and for quantification and monitoring of therapeutic anti-PD-L1 antibodies in patients.

SUMMARY OF THE INVENTION

In one aspect, the present invention provides for an isolated anti-idiotypic antibody that specifically binds to an anti-PD-L1 antibody. In some embodiments, the anti-PD-L1 antibody comprises:
(a) a light chain variable region comprising:
  (i) HVR-L1 comprising the amino acid sequence RASQDVSTAVA (SEQ ID NO:1);
  (ii) HVR-L2 comprising the amino acid sequence SASFLYS (SEQ ID NO:2); and
  (iii) HVR-L3 comprising the amino acid sequence QQYLYHPAT (SEQ ID NO:3); and
(b) a heavy chain variable region comprising:
  (i) HVR-H1 comprising the amino acid sequence GFTFSDSWIH (SEQ ID NO:4);
  (ii) HVR-H2 comprising the amino acid sequence AWISPYGGSTYYADSVKG (SEQ ID NO:5); and
  (iii) HVR-H3 comprising the amino acid sequence RHWPGGFDY (SEQ ID NO:6).

In some embodiments, the anti-PD-L1 antibody comprises a light chain variable region comprising the amino acid sequence of SEQ ID NO:7, and/or a heavy chain variable region comprising the amino acid sequence of SEQ ID NO:8.

In some embodiments, the anti-PD-L1 antibody comprises a light chain comprising the amino acid sequence of SEQ ID NO:9, and/or a heavy chain comprising the amino acid sequence of SEQ ID NO:10.

In some embodiments, the isolated anti-idiotypic antibody comprises a heavy chain variable region (VH) comprising HVR-H1 comprising the amino acid sequence of SEQ ID NO: 29, HVR-H2 comprising the amino acid sequence of SEQ ID NO: 30, and HVR-H3 comprising the amino acid sequence of SEQ ID NO: 31; and/or a light chain variable region (VL) comprising HVR-L1 comprising the amino acid sequence of SEQ ID NO: 11, HVR-L2 comprising the amino acid sequence of SEQ ID NO: 12, and HVR-L3 comprising the amino acid sequence of SEQ ID NO: 13.

In some embodiments, the isolated anti-idiotypic antibody comprises a VH comprising HVR-H1 comprising the amino acid sequence of SEQ ID NO: 32, HVR-H2 comprising the amino acid sequence of SEQ ID NO: 33, and HVR-H3 comprising the amino acid sequence of SEQ ID NO: 34; and/or a VL comprising HVR-L1 comprising the amino acid sequence of SEQ ID NO: 14, HVR-L2 comprising the amino acid sequence of SEQ ID NO: 15, and HVR-L3 comprising the amino acid sequence of SEQ ID NO: 16.

In some embodiments, the isolated anti-idiotypic antibody comprises a VH comprising HVR-H1 comprising the amino acid sequence of SEQ ID NO: 35, HVR-H2 comprising the amino acid sequence of SEQ ID NO: 36, and HVR-H3 comprising the amino acid sequence of SEQ ID NO: 34; and/or a VL comprising HVR-L1 comprising the amino acid sequence of SEQ ID NO: 14, HVR-L2 comprising the amino acid sequence of SEQ ID NO: 15, and HVR-L3 comprising the amino acid sequence of SEQ ID NO: 16.

In some embodiments, the isolated anti-idiotypic antibody comprises a heavy chain variable region comprising the sequence of SEQ ID NO:54 and/or a light chain variable region comprising the sequence of SEQ ID NO:53.

In some embodiments, the isolated anti-idiotyic antibody comprises a heavy chain comprising the sequence of SEQ ID NO: 60 and/or a light chain comprising the sequence of SEQ ID NO: 59.

In some embodiments, the isolated anti-idiotypic antibody comprises a VH comprising HVR-H1 comprising the amino acid sequence of SEQ ID NO: 37, HVR-H2 comprising the amino acid sequence of SEQ ID NO: 38, and HVR-H3 comprising the amino acid sequence of SEQ ID NO: 39; and/or a VL comprising HVR-L1 comprising the amino acid sequence of SEQ ID NO: 17, HVR-L2 comprising the amino acid sequence of SEQ ID NO: 18, and HVR-L3 comprising the amino acid sequence of SEQ ID NO: 19.

In some embodiments, the isolated anti-idiotypic antibody comprises a VH comprising HVR-H1 comprising the amino acid sequence of SEQ ID NO: 40, HVR-H2 comprising the amino acid sequence of SEQ ID NO: 41, and HVR-H3 comprising the amino acid sequence of SEQ ID NO: 42; and/or a VL comprising HVR-L1 comprising the amino acid sequence of SEQ ID NO: 20, HVR-L2 comprising the amino acid sequence of SEQ ID NO: 21, and HVR-L3 comprising the amino acid sequence of SEQ ID NO: 22.

In some embodiments, the isolated anti-idiotypic antibody comprises a VH comprising HVR-H1 comprising the amino acid sequence of SEQ ID NO: 43, HVR-H2 comprising the amino acid sequence of SEQ ID NO: 44, and HVR-H3 comprising the amino acid sequence of SEQ ID NO: 42; and/or a VL comprising HVR-L1 comprising the amino acid sequence of SEQ ID NO: 20, HVR-L2 comprising the amino acid sequence of SEQ ID NO: 21, and HVR-L3 comprising the amino acid sequence of SEQ ID NO: 22.

In some embodiments, the isolated anti-idiotypic antibody comprises a heavy chain variable region comprising the sequence of SEQ ID NO:56 and/or a light chain variable region comprising the sequence of SEQ ID NO:55.

In some embodiments, the isolated anti-idiotyic antibody comprises a heavy chain comprising the sequence of SEQ ID NO: 62 and/or a light chain comprising the sequence of SEQ ID NO: 61.

In some embodiments, the isolated anti-idiotypic antibody comprises a VH comprising HVR-H1 comprising the amino acid sequence of SEQ ID NO: 45, HVR-H2 comprising the amino acid sequence of SEQ ID NO: 46, and HVR-H3 comprising the amino acid sequence of SEQ ID NO: 47; and/or a VL comprising HVR-L1 comprising the amino acid sequence of SEQ ID NO: 23, HVR-L2 comprising the amino acid sequence of SEQ ID NO: 24, and HVR-L3 comprising the amino acid sequence of SEQ ID NO: 25.

In some embodiments, the isolated anti-idiotypic antibody comprises a VH comprising HVR-H1 comprising the amino acid sequence of SEQ ID NO: 48, HVR-H2 comprising the amino acid sequence of SEQ ID NO: 49, and HVR-H3 comprising the amino acid sequence of SEQ ID NO: 50; and/or a VL comprising HVR-L1 comprising the amino acid sequence of SEQ ID NO: 26, HVR-L2 comprising the amino acid sequence of SEQ ID NO: 27, and HVR-L3 comprising the amino acid sequence of SEQ ID NO: 28.

In some embodiments, the isolated anti-idiotypic antibody comprises a VH comprising HVR-H1 comprising the amino acid sequence of SEQ ID NO: 51, HVR-H2 comprising the amino acid sequence of SEQ ID NO: 52, and HVR-H3 comprising the amino acid sequence of SEQ ID NO: 50; and/or a VL comprising HVR-L1 comprising the amino acid sequence of SEQ ID NO: 26, HVR-L2 comprising the amino acid sequence of SEQ ID NO: 27, and HVR-L3 comprising the amino acid sequence of SEQ ID NO: 28.

In some embodiments, the isolated anti-idiotypic antibody comprises a heavy chain variable region comprising the sequence of SEQ ID NO:58 and/or a light chain variable region comprising the sequence of SEQ ID NO:57.

In some embodiments, the isolated anti-idiotyic antibody comprises a heavy chain comprising the sequence of SEQ ID NO: 64 and/or a light chain comprising the sequence of SEQ ID NO: 63.

In some embodiments, the isolated anti-idiotypic antibody specifically binds to at least one HVR of the anti-PD-L1 antibody.

In some embodiments, the isolated anti-idiotypic antibody is conjugated to a heterologous moiety or detectable moiety. In some embodiments, the detectable moiety is a label or biotin.

In another aspect, the invention provides for a composition comprising an anti-idiotypic antibody as provided herein.

In another aspect, the invention provides for a kit comprising a composition as provided herein.

In another aspect, the invention provides for an isolated nucleic acid encoding an anti-idiotypic antibody that specifically binds to an anti-PD-L1 antibody, wherein the anti-idiotypic antibody comprises a heavy chain variable region comprising HVR-H1, HVR-H2 and HVR-H3 and a light chain variable region comprising HVR-L1, HVR-L2 and HVR-L3, wherein:
(a) HVR-H1 comprises the amino acid sequence SYDMS (SEQ ID NO:35);
(b) HVR-H2 comprises the amino acid sequence YIS-SGGGSTYYPDTVKG (SEQ ID NO:36);
(c) HVR-H3 comprises the amino acid sequence LVYYDYDDAMDY (SEQ ID NO:34);
(d) HVR-L1 comprises the amino acid sequence SASSSVSYMH; (SEQ ID NO:14);
(e) HVR-L2 comprises the amino acid sequence STSNLAS (SEQ ID NO: 15); and
(f) HVR-L3 comprises the amino acid sequence QQRSSYPPTF (SEQ ID NO:16).

In another aspect, the invention provides for an isolated nucleic acid encoding an anti-idiotypic antibody that specifically binds to an anti-PD-L1 antibody, wherein the anti-idiotypic antibody comprises a heavy chain variable region comprising HVR-H1, HVR-H2 and HVR-H3 and a light chain variable region comprising HVR-L1, HVR-L2 and HVR-L3, wherein:
(a) HVR-H1 comprises the amino acid sequence DYIML (SEQ ID NO:43);
(b) HVR-H2 comprises the amino acid sequence NINPYYGSTSYNLKFKG (SEQ ID NO:44);
(c) HVR-H3 comprises the amino acid sequence WGG-NYEGWFAY (SEQ ID NO:42);
(d) HVR-L1 comprises the amino acid sequence HASQGISSNIG; (SEQ ID NO:20);
(e) HVR-L2 comprises the amino acid sequence HGTNLED (SEQ ID NO:21); and
(f) HVR-L3 comprises the amino acid sequence VQYAQFPLTF (SEQ ID NO:22).

In another aspect, the invention provides for an isolated nucleic acid encoding an anti-idiotypic antibody that specifically binds to an anti-PD-L1 antibody, wherein the anti-idiotypic antibody comprises a heavy chain variable region comprising HVR-H1, HVR-H2 and HVR-H3 and a light chain variable region comprising HVR-L1, HVR-L2 and HVR-L3, wherein:
(a) HVR-H1 comprises the amino acid sequence SYDMS (SEQ ID NO:51);
(b) HVR-H2 comprises the amino acid sequence YIS-SGGGSTYYPDTVKG (SEQ ID NO:52);
(c) HVR-H3 comprises the amino acid sequence TIYYGYDDVMDY (SEQ ID NO:50);
(d) HVR-L1 comprises the amino acid sequence SASSSVSYMH; (SEQ ID NO:26);
(e) HVR-L2 comprises the amino acid sequence STSNLAS (SEQ ID NO:27); and
(f) HVR-L3 comprises the amino acid sequence QQRSGYPPTF (SEQ ID NO:28).

In another aspect, the invention provides for an isolated nucleic acid encoding an anti-idiotypic antibody as provided herein.

In another aspect, the invention provides for a vector comprising a nucleic acid as provided herein.

In another aspect, the invention provides for a host cell comprising a vector as provided herein.

In some embodiments, the host cell is eukaryotic. In some embodiments, the host cell is mammalian. In some embodiments, the host cell is a Chinese Hamster Ovary (CHO) cell.

In some embodiments, the host cell is prokaryotic. In some embodiments, the host cell is *E. coli*.

In another aspect, the invention provides for a process for making an anti-idiotypic antibody comprising culturing a host cell as provided herein under conditions suitable for the expression of the vector encoding the anti-idiotypic antibody and recovering the anti-idiotypic antibody.

In another aspect, the invention provides for a method for detecting in a biological sample an anti-PD-L1 antibody comprising:
(a) contacting the biological sample with a capture agent, wherein the capture agent is a composition comprising an anti-idiotypic antibody as provided herein, thereby forming an immunocomplex;
(b) contacting the immunocomplex from (a) with a detectable antibody that binds to the anti-PD-L1 antibody; and
(c) measuring the level of the anti-PD-L1 antibody bound to the composition by detecting the detectable antibody.

In another aspect, the invention provides for a method for detecting in a biological sample an anti-PD-L1 antibody comprising:
(a) contacting the biological sample with a capture agent, wherein the capture agent is an anti-idiotypic antibody as provided herein that binds the anti-PD-L1 antibody present in the sample, thereby forming an immunocomplex;
(b) contacting the immunocomplex from (a) with a detectable antibody that binds to the anti-PD-L1 antibody; and
(c) measuring the level of the anti-PD-L1 antibody bound to the anti-idiotypic antibody by detecting the detectable antibody.

In some embodiments, the anti-idiotypic antibody is immobilized to a solid support and the method further comprises the step of separating the biological sample from the immobilized anti-idiotypic antibody bound to the anti-PD-L1 antibody.

In some embodiments, the immobilized anti-idiotypic antibody is conjugated to biotin and bound to a streptavidin coated microtiter plate.

In some embodiments, the detectable antibody is an antibody from a non-human species that binds to human or humanized antibodies.

In some embodiments, the detectable antibody is directly detectable, or is conjugated to horseradish peroxidase, or is detected by a fluorometric or calorimetric reagent.

In some embodiments, the biological sample is isolated from a human subject.

In some embodiments, the human subject has been treated with an anti-PD-L1 antibody comprising:
(a) a light chain variable region comprising:
(i) HVR-L1 comprising the amino acid sequence RASQDVSTAVA (SEQ ID NO:1);
(ii) HVR-L2 comprising the amino acid sequence SASFLYS (SEQ ID NO:2);
(iii) HVR-L3 comprising the amino acid sequence QQYLYHPAT (SEQ ID NO:3); and
(b) a heavy chain variable region comprising:
(i) HVR-H1 comprising the amino acid sequence GFTFSDSWIH (SEQ ID NO:4);
(ii) HVR-H2 comprising the amino acid sequence AWISPYGGSTYYADSVKG (SEQ ID NO:5);
(iii) HVR-H3 comprising the amino acid sequence RHWPGGFDY (SEQ ID NO:6).

In some embodiments, the method further comprises using a standard curve to determine the level of the anti-PD-L1 antibody compared to a known level of the anti-PD-L1 antibody.

In some embodiments, the biological sample is blood, plasma or serum.

In another aspect, the invention provides for an immunoassay kit for specifically detecting an anti-PD-L1 antibody in a biological sample, comprising:
(a) an anti-idiotypic antibody of as provided herein or a composition as provided herein;
(b) a detectable antibody that binds to the anti-PD-L1 antibody; and
(c) instructions for detecting said anti-PD-L1 antibody. In some embodiments, the kit is useful in an immunoassay for detecting the anti-PD-L1 antibody.

In another aspect, the invention provides for a method for detecting an anti-PD-L1 antibody in a biological sample, comprising:
(a) contacting the biological sample with an anti-idiotypic antibody as provided herein or a composition as provided herein under a condition to allow binding of the anti-idiotypic antibody to the anti-PD-L1 antibody to form a complex;
(b) analyzing the sample by Immunofixation Electrophoresis to compare the sample contacted with the anti-idiotypic antibody to the sample that has not been contacted with the anti-idiotypic antibody;
(c) detecting the presence of the anti-PD-L1 antibody in the biological sample; wherein a difference in the migration between the sample contacted with the anti-idiotypic antibody and the sample that has not been contacted with the anti-idiotypic antibody indicates the presence of the anti-PD-L1 antibody in the biological sample.

In another aspect, the invention provides for a method for detecting M-protein in a biological sample comprising:
(a) contacting the biological sample with an anti-idiotypic antibody as provided herein or a composition as provided herein under a condition to allow binding of the anti-idiotypic antibody to the anti-PDL1 antibody to form a complex;
(b) analyzing the sample by Immunofixation Electrophoresis to compare the sample contacted with the anti-idiotypic antibody to the sample that has not been contacted with the anti-idiotypic antibody; and
(c) detecting the presence of M-protein in the biological sample. In some embodiments, step (b) results in separation of the complex of the anti-PD-L1 antibody and the anti-idiotypic antibody from the M-protein. In some embodiments, before step (c), the method further comprises the step of determining if a band is M-protein or not by determining if its migration is affected by the addition of the anti-idiotypic antibody. In some embodiments, the biological sample is blood, urine or serum.

In another aspect, the invention provides for a method for monitoring the effectiveness of an anti-PD-L1 antibody treatment in a subject comprising:
(a) contacting a biological sample with an anti-idiotypic antibody as provided herein or a composition as provided herein under a condition to allow binding of the anti-idiotypic antibody to the anti-PD-L1 antibody to form a complex; wherein the biological sample is from the subject, and wherein the subject has multiple myeloma and has been treated with the anti-PD-L1 antibody;

(b) analyzing the sample by Immunofixation Electrophoresis to compare the sample contacted with the anti-idiotypic antibody to the sample that has not been contacted with the anti-idiotypic antibody;

(c) detecting the presence of the anti-PD-L1 antibody in the biological sample, wherein a difference in the migration between the sample contacted with the anti-idiotypic antibody and the sample that has not been contacted with the anti-idiotypic antibody indicates the presence of the anti-PD-L1 antibody in the biological sample; and (d) detecting the level of M-protein in the biological sample; wherein the level of the M-protein in the biological sample indicates the effectiveness of the anti-PD-L1 antibody treatment. In some embodiments, step (b) results in separation of the complex of the anti-PD-L1 antibody and the anti-idiotypic antibody from the M-protein. In some embodiments, before step (d), the method further comprises the step of determining if a band is M-protein or not by determining if its migration is affected by the addition of the anti-idiotypic antibody. In some embodiments, the biological sample is blood, urine, or serum.

It is to be understood that one, some, or all of the properties of the various embodiments described herein may be combined to form other embodiments of the present invention.

BRIEF DESCRIPTION OF THE FIGURES

FIG. 1 shows an amino acid sequence alignment of the heavy chain variable region (VH) of anti-idiotypic antibody 105D11 (SEQ ID NO:54), 43B5 (SEQ ID NO:56) and 48C1 (SEQ ID NO:58). The heavy chain contact CDR, Chothia CDR, and Kabat CDR sequences are indicated.

FIG. 2 shows amino acid sequence alignment of the light chain variable region (VL) of anti-idiotypic antibody 105D11 (SEQ ID NO:53), 43B5 (SEQ ID NO:55) and 48C1 (SEQ ID NO:57). The light chain contact CDR, Chothia CDR, and Kabat CDR sequences are indicated.

FIG. 3 shows SPR generated kinetics ($k_a$, $k_d$, and $K_D$) for antibody 105D11 binding to anti-PDL1 antibody Fab and antibody YW167B.43 (a framework control Fab).

FIG. 4 shows SPR generated kinetics ($k_a$, $k_d$, and $K_D$) for antibody 43B5 binding to anti-PDL1 antibody Fab and antibody YW167B.43 (a framework control Fab).

FIG. 7 shows IgA/Ig kappa M protein spike in the serum of a multiple myeloma patient (Panel 1, lane A and lane K) detected with high resolution on an IFE assay. Patient 'MM5' serum was pre-incubated for 2 hours in the following conditions: atezolizumab anti-idiotypic mouse mAB clone 48C1 alone spiked in at 1500 µg/ml (Panel 2), atezolizumab alone spiked in at 1500 µg/ml (Panel 3, lane G and lane K), and atezolizumab+atezolizumab anti-idiotype clone 48C1 added together at 1500 µg/ml each (Panel 4).

DETAILED DESCRIPTION OF EMBODIMENTS OF THE INVENTION

I. Definitions

Figure 5:
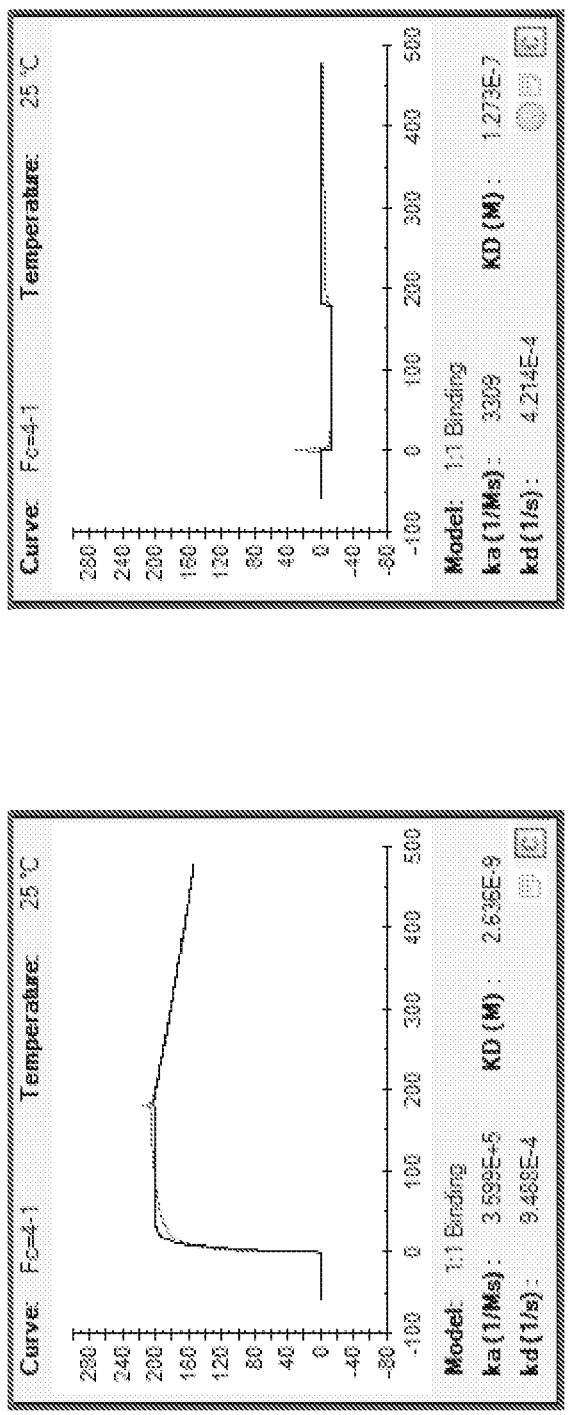
FIG. 5 shows SPR generated kinetics ($k_a$, $k_d$, and $K_D$) for antibody 48C1 binding to anti-PDL1 antibody Fab and antibody YW167B.43 (a framework control Fab).

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described herein.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The terms "anti-PD-L1 antibody", "anti-PD-L1", "PD-L1 antibody" or "an antibody that binds to PD-L1" refers to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an antibody that binds to PD-L1 has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-PD-L1 antibody binds to an epitope of PD-L1 that is conserved among PD-L1 from different species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "chimeric" antibody refers to an antibody in which a portion of the heavy and/or light chain is derived from a particular source or species, while the remainder of the heavy and/or light chain is derived from a different source or species.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "detecting" is used in the broadest sense to include both qualitative and quantitative measurements of a target molecule. In one aspect, the detecting method as described herein is used to identify the mere presence of the antibody of interest in a biological sample. In another aspect, the method is used to test whether the antibody of interest in a sample is present at a detectable level. In yet another aspect, the method can be used to quantify the amount of the antibody of interest in a sample and further to compare the antibody levels from different samples.

The term "biological sample" refers to any biological substance that may contain an antibody of interest. A sample can be biological fluid, such as whole blood or whole blood components including red blood cells, white blood cells, platelets, serum and plasma, ascites, itreous fluid, lymph fluid, synovial fluid, follicular fluid, seminal fluid, amniotic fluid, milk, saliva, sputum, tears, perspiration, mucus, cerebrospinal fluid, and other constituents of the body that may contain the antibody of interest. In various embodiments, the sample is a body sample from any animal. In some embodiments, the sample is from a mammal. In some embodiments, the sample is from a human subject. In some embodiments, the biological sample is from clinical patients or patients treated with a therapeutic anti-PD-L1 antibody or antibodies. In certain embodiments, the biological sample is serum or plasma. In certain embodiments, the biological sample is serum from a clinical patient.

The term "capture reagent" refers to a reagent (e.g., an antibody) or mixture of such reagent that bind to a target (e.g., antibody) of interest and are capable of binding and capturing the target (e.g., antibody) of interest in a biological sample such that under suitable conditions, the complex of capture reagent and target (e.g., antibody) of interest can be separated from the rest of the sample. For example, a capture reagent can be an anti-idiotypic antibody or mixture of such antibodies that bind an idiotype of the antibody of interest and are capable of binding and capturing the antibody of interest in a biological sample such that under suitable conditions, the complex of capture reagent and antibody of interest can be separated from the rest of the sample. In certain embodiments, the capture reagent is immobilized or immobilizable.

An "anti-idiotypic antibody," as used herein, is an antibody that binds to the VH and/or VL domain of the cognate antibody, in this case the antibody of interest. Typically, such anti-idiotypic antibodies are prepared by immunizing a mammal such as a mouse with the antibody of interest and producing a hybridoma library and selecting from the panel of antibodies derived from the hybridomas those antibodies that give a clean signal in the assay, whether for the capture reagent or the detectable antibody. In certain embodiments, the anti-idiotypic antibody is immobilized or immobilizable. In some embodiments, anti-idiotypic antibodies are monoclonal antibodies and can be for example, rodent antibodies such as murine or rat antibodies.

An "anti-PD-L1 idiotypic antibody," as used herein, is one that specifically binds to an anti-PD-L1 monoclonal antibody with sufficient specificity and affinity to be useful in detection of the anti-PD-L1 antibody.

The term "detectable antibody" refers to an antibody that binds the antibody of interest and is capable of being detected either directly through a label amplified by a detection means, or indirectly through, e.g., another antibody that is labeled. In some embodiments, the detectable antibody is an antibody from a non-human species that binds to human antibodies. In some embodiments, the detectable antibody is an anti-idiotypic antibody or mixture of such antibodies that bind an idiotype of the antibody of interest. For direct labeling, the antibody is typically conjugated to a moiety that is detectable by some means. In some embodiments, the detectable antibody is conjugated to horseradish peroxidase.

The term "detection means" refers to a moiety or technique used to detect the presence of the detectable antibody through signal reporting that is then read out in the assay herein. It includes reagents that amplify the immobilized label such as the label captured onto a microtiter plate.

The "Fab" fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-idiotypic antibody" refers to one or more nucleic acid molecules encoding the heavy and light chains (or fragments thereof) of an anti-idiotypic antibody, including such nucleic acid molecule(s) in a single vector or separate vectors, and such nucleic acid molecule(s) present at one or more locations in a host cell.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects.

A "signature peptide" of an anti-PD-L1 antibody refers to a proteolytic peptide (e.g., a tryptic peptide) that is exclusively present in one antibody isotype.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" or an "effective amount" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the singular form "a", "an", and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

It is understood that aspect and embodiments of the invention described herein include "comprising," "consisting," and "consisting essentially of" aspects and embodiments.

II. Compositions and Methods

In one aspect, the invention provides anti-idiotypic antibodies that specifically bind to an anti-PD-L1 monoclonal antibody. Antibodies of the invention are useful, e.g., for the detection and/or quantification of anti-PD-L1 in biological samples, for example, in clinical samples. In some embodiments, the anti-PD-L1 antibody is monoclonal, chimeric, humanized or human.

A. Anti-PD-L1 Antibodies i. Exemplary Anti-PD-L1 Antibodies

In certain embodiments, an anti-idiotypic antibody binds to an anti-PD-L1 antibody comprising (a) a light chain variable region comprising HVR-L1 comprising the amino acid sequence RASQDVSTAVA (SEQ ID NO:1), HVR-L2 comprising the amino acid sequence SASFLYS (SEQ ID NO:2), and HVR-L3 comprising the amino acid sequence QQYLYHPAT (SEQ ID NO:3); and (b) a heavy chain variable region comprising HVR-H1 comprising the amino acid sequence GFTFSDSWIH (SEQ ID NO:4), HVR-H2 comprising the amino acid sequence AWISPYGGSTYYADSVKG (SEQ ID NO:5) and HVR-H3 comprising the amino acid sequence RHWPGGFDY (SEQ ID NO:6).

In some embodiments, the anti-PD-L1 antibody comprises a light chain variable region comprising the amino acid sequence of SEQ ID NO:7, and a heavy chain variable region comprising the amino acid sequence of SEQ ID NO:8. In some embodiments, the anti-PD-L1 antibody comprises a light chain variable region having at least 85%, 86%, 87%, 88%, 89%, 90%, 91%, 92%, 93%, 94%, 95%, 96%, 97%, 98%, or 99% sequence identity to the light chain variable region having the amino acid sequence of SEQ ID NO:7, and/or a heavy chain variable region having at least 85%, 86%, 87%, 88%, 89%, 90%, 91%, 92%, 93%, 94%, 95%, 96%, 97%, 98%, or 99% identity to the heavy chain variable region having the amino acid sequence of SEQ ID NO:8.

In some embodiments, the anti-PD-L1 antibody comprises a light chain comprising the amino acid sequence of SEQ ID NO:9, and a heavy comprising the amino acid sequence of SEQ ID NO: 10. In some embodiments, the anti-PD-L1 antibody comprises a light chain having at least 85%, 86%, 87%, 88%, 89%, 90%, 91%, 92%, 93%, 94%, 95%, 96%, 97%, 98%, or 99% sequence identity to the light chain having the amino acid sequence of SEQ ID NO:9, and a heavy chain having at least 85%, 86%, 87%, 88%, 89%, 90%, 91%, 92%, 93%, 94%, 95%, 96%, 97%, 98%, or 99% identity to the heavy chain having the amino acid sequence of SEQ ID NO:10.

In some embodiments, the anti-PD-L1 antibody is atezolizumab (TECENTRIQ®).

In some embodiments, the anti-PD-L1 antibody comprises the HVRs of atezolizumab. In some embodiments, the anti-PD-L1 antibody comprises the heavy chain variable region and/or the light chain variable region of atezolizumab.

In some embodiments, the anti-PD-L1 antibody is monoclonal, chimeric or humanized.

Anti-PD-L1 Antibody Light Chain Variable Region Amino Acid Sequence

```
                                          (SEQ ID NO: 7)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR
```

Anti-PD-L1 Antibody Heavy Chain Variable Region Amino Acid Sequence

```
                                          (SEQ ID NO: 8)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK
```

Anti-PD-L1 Antibody Light Chain Amino Acid Sequence

```
                                          (SEQ ID NO: 9)
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC
```

Anti-PD-L1 Antibody Heavy Chain Amino Acid Sequence

```
                                          (SEQ ID NO: 10)
EVQLVESGGGLVQPGGSLRLSCAASGFTFSDSWIHWVRQAPGKGLEW

VAWISPYGGSTYYADSVKGRFTISADTSKNTAYLQMNSLRAEDTAVY

YCARRHWPGGFDYWGQGTLVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDG

VEVHNAKTKPREEQYASTYRVVSVLTVLHQDWLNGKEYKCKVSNKAL

PAPIEKTISKAKGQPREPQVYTLPPSREEMTKNQVSLTCLVKGFYPS

DIAVEWESNGQPENNYKTTPPVLDSDGSFFLYSKLTVDKSRWQQGNV

FSCSVMHEALHNHYTQKSLSLSPG
```

B. Anti-Idiotypic Antibodies i. Exemplary Anti-Idiotypic Antibodies

In one aspect, the invention provides anti-idiotypic antibodies that specifically bind to an anti-PD-L1 antibody described herein. In some embodiments, the anti-idiotypic antibody binds an anti-PD-L1 antibody, wherein the anti-PD-L1 antibody comprises (a) a light chain variable region comprising HVR-L1 comprising the amino acid sequence RASQDVSTAVA (SEQ ID NO:1), HVR-L2 comprising the amino acid sequence SASFLYS (SEQ ID NO:2), and HVR-L3 comprising the amino acid sequence QQYLYHPAT (SEQ ID NO:3); and (b) a heavy chain variable region comprising HVR-H1 comprising the amino acid sequence GFTFSDSWIH (SEQ ID NO:4), HVR-H2 comprising the amino acid sequence AWISPYGGSTYYADSVKG (SEQ ID NO:5), and HVR-H3 comprising the amino acid sequence RHWPGGFDY (SEQ ID NO:6). In some embodiments, the anti-idiotypic antibody specifically binds to at least one, at least two, at least three, at least four, at least five or six HVRs of the anti-PD-L1 antibody.

In some embodiments, the anti-idiotypic antibody comprises one, two, three, four, five, or six HVRs (Kabat) of antibody 105D11 as shown in FIGS. 1 and 2. In some embodiments, the anti-idiotypic antibody comprises the VH and/or the VL of antibody 105D11 as shown in FIGS. 1 and 2.

In some embodiments, the anti-idiotypic antibody comprises a heavy chain variable doman (VH) sequence having at least 90%, 91%, 92%, 93%, 94%, 95%, 96%, 97%, 98%, 99%, or 100% sequence identity to the amino acid sequence of SEQ ID NO: 54. In certain embodiments, a VH sequence having at least 90%, 91%, 92%, 93%, 94%, 95%, 96%, 97%, 98%, 99%, or 100% sequence identity to the amino acid sequence of SEQ ID NO: 54 contains substitutions (e.g., conservative substitutions), insertions, or deletions relative to the reference sequence, but an anti-PD-L1 idiotypic antibody comprising that VH sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 54. In certain embodiments, substitutions, insertions, or deletions occur in regions outside the HVRs (i.e., in the FRs). Optionally, the anti-PD-L1 idiotypic antibody comprises the VH sequence of SEQ ID NO: 54 including post-translational modifications of that sequence. In a particular embodiment, the VH comprises one, two or three HVRs selected from: (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 34.

In another aspect, an anti-PD-L1 idiotypic antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 53. In certain embodiments, a VL sequence having at least 90%, 91%, 92%, 93%, 94%, 95%, 96%, 97%, 98%, 99%, or 100% sequence identity to the amino acid sequence of SEQ ID NO: 53 contains substitutions (e.g., conservative substitutions), insertions, or deletions relative to the reference sequence, but an anti-PD-L1 idiotypic antibody comprising that VL sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 53. In certain embodiments, the substitutions, insertions, or deletions occur in regions outside the HVRs (i.e., in the FRs). Optionally, the anti-PD-L1 idiotypic antibody comprises the VL sequence of SEQ ID NO: 53, including post-translational modifications of that sequence. In a particular embodiment, the VL comprises one, two or three HVRs selected from (a) HVR-L1 comprising the amino acid sequence of SEQ ID NO: 14; (b) HVR-L2 comprising the amino acid sequence of SEQ ID NO: 15; and (c) HVR-L3 comprising the amino acid sequence of SEQ ID NO: 16.

In another aspect, an anti-PD-L1 idiotypic antibody is provided, wherein the antibody comprises a VH as in any of the embodiments provided above, and a VL as in any of the embodiments provided above. In one embodiment, the antibody comprises the VH sequence of SEQ ID NO: 54 and the VL sequence of SEQ ID NO: 53, including post-translational modifications of those sequences.

In some embodiments, an anti-PD-L1 idiotypic antibody is provided, wherein the antibody comprises a VH comprising HVR-H1 comprising the amino acid sequence of SEQ ID NO: 29, HVR-H2 comprising the amino acid sequence of SEQ ID NO: 30, and HVR-H3 comprising the amino acid sequence of SEQ ID NO: 31; and a VL comprising HVR-L1 comprising the amino acid sequence of SEQ ID NO: 11, HVR-L2 comprising the amino acid sequence of SEQ ID NO: 12; and HVR-L3 comprising the amino acid sequence of SEQ ID NO: 13. In some embodiments, the antibody comprises a VH comprising HVR-H1 comprising the amino acid sequence of SEQ ID NO: 32, HVR-H2 comprising the amino acid sequence of SEQ ID NO: 33, and HVR-H3 comprising the amino acid sequence of SEQ ID NO: 34; and a VL comprising HVR-L1 comprising the amino acid sequence of SEQ ID NO: 14, HVR-L2 comprising the amino acid sequence of SEQ ID NO: 15; and HVR-L3 comprising the amino acid sequence of SEQ ID NO: 16. In some embodiments, the antibody comprises a VH comprising HVR-H1 comprising the amino acid sequence of SEQ ID NO: 35, HVR-H2 comprising the amino acid sequence of SEQ ID NO: 36, and HVR-H3 comprising the amino acid sequence of SEQ ID NO: 34; and a VL comprising HVR-L1 comprising the amino acid sequence of SEQ ID NO: 14, HVR-2 comprising the amino acid sequence of SEQ ID NO: 15; and HVR-L3 comprising the amino acid sequence of SEQ ID NO: 16.

In another aspect, the anti-idiotypic antibody comprises one, two, three, four, five, or six HVRs (e.g., Kabat) of antibody 43B5 as shown in FIGS. 1 and 2. In some embodiments, the anti-idiotypic antibody comprises the VH and/or the VL of antibody 43B5 as shown in FIGS. 1 and 2.

In another aspect, an anti-PD-L1 idiotypic antibody comprises a heavy chain variable doman (VH) sequence having at least 90%, 91%, 92%, 93%, 94%, 95%, 96%, 97%, 98%, 99%, or 100% sequence identity to the amino acid sequence of SEQ ID NO: 56. In certain embodiments, a VH sequence having at least 90%, 91%, 92%, 93%, 94%, 95%, 96%, 97%, 98%, 99%, or 100% sequence identity to the amino acid sequence of SEQ ID NO: 56 contains substitutions (e.g., conservative substitutions), insertions, or deletions relative to the reference sequence, but an anti-PD-L1 idiotypic antibody comprising that VH sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 56. In certain embodiments, substitutions, insertions, or deletions occur in regions outside the HVRs (i.e., in the FRs). Optionally, the anti-PD-L1 idiotypic antibody comprises the VH sequence of SEQ ID NO: 56 including post-translational modifications of that sequence. In a particular embodiment, the VH comprises one, two or three HVRs selected from: (a) HVR-H1 comprising the amino acid sequence of SEQ ID NO: 43, (b) HVR-H2 comprising the amino acid sequence of SEQ ID NO: 44, and (c) HVR-H3 comprising the amino acid sequence of SEQ ID NO: 42.

In another aspect, an anti-PD-L1 idiotypic antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, 99%, or 100% sequence identity to the amino acid sequence of SEQ ID NO: 55 contains substitutions (e.g., conservative substitutions), insertions, or deletions relative to the reference sequence, but an anti-PD-L1 idiotypic antibody comprising that VL sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 55. In certain embodiments, the substitutions, insertions, or deletions occur in regions outside the HVRs (i.e., in the FRs). Optionally, the anti-PD-L1 idiotypic antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 20; (b) HVR-L2 comprising the amino acid sequence of SEQ ID NO: 21; and (c) HVR-L3 comprising the amino acid sequence of SEQ ID NO: 22.

In another aspect, an anti-PD-L1 idiotypic antibody is provided, wherein the antibody comprises a VH as in any of the embodiments provided above, and a VL as in any of the embodiments provided above. In one embodiment, the antibody comprises the VH and VL sequences in SEQ ID NO: 56 and SEQ ID NO: 55, respectively, including post-translational modifications of those sequences.

In some embodiments, an anti-PD-L1 idiotypic antibody is provided, wherein the antibody comprises a VH comprising HVR-H1 comprising the amino acid sequence of SEQ ID NO: 37, HVR-H2 comprising the amino acid sequence of SEQ ID NO: 38, and HVR-H3 comprising the amino acid sequence of SEQ ID NO: 39; and a VL comprising HVR-L1 comprising the amino acid sequence of SEQ ID NO: 17, HVR-L2 comprising the amino acid sequence of SEQ ID NO: 18, and HVR-L3 comprising the amino acid sequence of SEQ ID NO: 19. In some embodiments, the antibody comprises a VH comprising HVR-H1 comprising the amino acid sequence of SEQ ID NO: 40, HVR-H2 comprising the amino acid sequence of SEQ ID NO: 41, and HVR-H3 comprising the amino acid sequence of SEQ ID NO: 42; and a VL comprising HVR-L1 comprising the amino acid sequence of SEQ ID NO: 20, HVR-L2 comprising the amino acid sequence of SEQ ID NO: 21, and HVR-L3 comprising the amino acid sequence of SEQ ID NO: 22. In some embodiments, the antibody comprises a VH comprising HVR-H1 comprising the amino acid sequence of SEQ ID NO: 43, HVR-H2 comprising the amino acid sequence of SEQ ID NO: 44, and HVR-H3 comprising the amino acid sequence of SEQ ID NO: 42; and a VL comprising HVR-L1 comprising the amino acid sequence of SEQ ID NO: 20, HVR-L2 comprising the amino acid sequence of SEQ ID NO: 21, and HVR-L3 comprising the amino acid sequence of SEQ ID NO: 22.

In some embodiments, the anti-idiotypic antibody comprises one, two, three, four, five, or six HVRs (e.g., Kabat) of antibody 48C1 as shown in FIGS. 1 and 2. In some embodiments, the anti-idiotypic antibody comprises the VH and/or the VL of antibody 48C1 as shown in FIGS. 1 and 2.

In another aspect, an anti-PD-L1 idiotypic antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 58. In certain embodiments, a VH sequence having at least 90%, 91%, 92%, 93%, 94%, 95%, 96%, 97%, 98%, 99%, or 100% sequence identity to the amino acid sequence of SEQ ID NO: 58 contains substitutions (e.g., conservative substitutions), insertions, or deletions relative to the reference sequence, but an anti-PD-L1 idiotypic antibody comprising that VH sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 58. In certain embodiments, substitutions, insertions, or deletions occur in regions outside the HVRs (i.e., in the FRs). Optionally, the anti-PD-L1 idiotypic antibody comprises the VH sequence of SEQ ID NO: 58 including post-translational modifications of that sequence. In a particular embodiment, the VH comprises one, two or three HVRs selected from: (a) HVR-H1 comprising the amino acid sequence of SEQ ID NO: 51, (b) HVR-H2 comprising the amino acid sequence of SEQ ID NO: 52, and (c) HVR-H3 comprising the amino acid sequence of SEQ ID NO: 50.

In another aspect, an anti-PD-L1 idiotypic antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, 99%, or 100% identity to the amino acid sequence of SEQ ID NO: 57 contains substitutions (e.g., conservative substitutions), insertions, or deletions relative to the reference sequence, but an anti-PD-L1 idiotypic antibody comprising that VL sequence retains the ability to bind to the same anti-PD-L1 antibody as the anti-idiotypic antibody comprising the reference sequence. In certain embodiments, a total of 1 to 10 amino acids have been substituted, inserted and/or deleted in SEQ ID NO: 57. In certain embodiments, the substitutions, insertions, or deletions occur in regions outside the HVRs (i.e., in the FRs). Optionally, the anti-PD-L1 idiotypic antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 26; (b) HVR-L2 comprising the amino acid sequence of SEQ ID NO: 27; and (c) HVR-L3 comprising the amino acid sequence of SEQ ID NO: 28.

In another aspect, an anti-PD-L1 idiotypic antibody is provided, wherein the antibody comprises a VH as in any of the embodiments provided above, and a VL as in any of the embodiments provided above. In one embodiment, the antibody comprises the VH and VL sequences in SEQ ID NO: 58 and SEQ ID NO: 57, respectively, including post-translational modifications of those sequences.

In some embodiments, an anti-PD-L1 idiotypic antibody is provided, wherein the antibody comprises a VH comprising HVR-H1 comprising the amino acid sequence of SEQ ID NO: 45, HVR-H2 comprising the amino acid sequence of SEQ ID NO: 46, and HVR-H3 comprising the amino acid sequence of SEQ ID NO: 47; and a VL comprising HVR-L1 comprising the amino acid sequence of SEQ ID NO: 23, HVR-L2 comprising the amino acid sequence of SEQ ID NO: 24, and HVR-L3 comprising the amino acid sequence of SEQ ID NO: 25. In some embodiments, the antibody comprises a VH comprising HVR-H1 comprising the amino acid sequence of SEQ ID NO: 48, HVR-H2 comprising the amino acid sequence of SEQ ID NO: 49, and HVR-H3 comprising the amino acid sequence of SEQ ID NO: 50; and a VL comprising HVR-L1 comprising the amino acid sequence of SEQ ID NO: 26, HVR-L2 comprising the amino acid sequence of SEQ ID NO: 27, and HVR-L3 comprising the amino acid sequence of SEQ ID NO: 28. In some embodiments, the antibody comprises a VH comprising HVR-H1 comprising the amino acid sequence of SEQ ID NO: 51, HVR-H2 comprising the amino acid sequence of SEQ ID NO: 52, and HVR-H3 comprising the amino acid sequence of SEQ ID NO: 50; and a VL comprising HVR-L1 comprising the amino acid sequence of SEQ ID NO: 26, HVR-L2 comprising the amino acid sequence of SEQ ID NO: 27, and HVR-L3 comprising the amino acid sequence of SEQ ID NO: 28.

In a further aspect of the invention, an anti-PD-L1 idiotypic antibody according to any of the above embodiments is a monoclonal antibody, including a chimeric, humanized or human antibody. In one embodiment, an anti-PD-L1 idiotypic antibody is an antibody fragment, e.g., a Fv, Fab, Fab', scFv, diabody, or F(ab')$_2$ fragment. In another embodiment, the anti-PD-L1 idiotypic antibody is a full length antibody, e.g., an intact IgG 1 antibody or other antibody class or isotype as defined herein.

In a further aspect of the invention, an anti-PD-L1 idiotypic antibody according to any of the above embodiments or described herein is conjugated to a heterologous moiety or agent.

In another aspect, provided herein is a composition comprising one or more of the anti-PD-L1 idiotypic antibodies according to any of the above embodiments or described herein. Also provided herein is a nucleic acid encoding the anti-idiotypic antibodies described herein, a vector comprising the nucleic acid, and a host cell comprising the vector. In some embodiments, the host cell is isolated or purified. In some embodiments, the host cell is a cell culture medium.

ii. Methods of Production

A description follows as to exemplary techniques for the production of the anti-idiotypic antibodies used in accordance with the present invention.

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include anti-PD-L1, an antigen binding fragment thereof, or fusion proteins thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-idiotypic antibody titer. If desired, the mammal can be boosted until the antibody titer increases or plateaus.

2. Monoclonal Antibodies

The antibodies of the invention may alternatively be monoclonal antibodies. Monoclonal antibodies may be made using the hybridoma method first described by Kohler et al., Nature, 256:495 (1975), or may be made by recombinant DNA methods (see, e.g. U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Fusion partner myeloma cells are those that fuse efficiently, support stable high-level production of antibody by the selected antibody-producing cells, and are sensitive to a selective medium that selects against the unfused parental cells. Myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107: 220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994).

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Screening of the libraries can be accomplished by various techniques known in the art. For example, anti-PD-L1 can be used to coat the wells of adsorption plates, expressed on host cells affixed to adsorption plates or used in cell sorting, or conjugated to biotin for capture with streptavidin-coated beads, or used in any other method for panning display libraries.

The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

Any of the anti-idiotypic antibodies of the invention can be obtained by designing a suitable antigen screening procedure to select for the phage clone of interest followed by construction of a full length anti-idiotypic antibody clone using the Fv sequences from the phage clone of interest and suitable constant region (Fe) sequences described in Kabat et al., Sequences of Proteins of Immunological Interest, Fifth Edition, NIH Publication 91-3242, Bethesda Md. (1991), vols. 1-3.

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |

TABLE 1-continued

| Original Residue | Exemplary Substitutions | Preferred Substitutions |
|---|---|---|
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
hydrophobic: Norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Afol. Biol. 207: 179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

4. Recombinant Methods and Compositions

Antibodies may be produced using recombinant methods and compositions, e.g., as described in U.S. Pat. No. 4,816,567. In one embodiment, isolated nucleic acid encoding an anti-idiotypic antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-PD-L1 idiotypic antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-PD-L1 idiotypic antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Afolecular Biology, Vol. 248 (B.K.C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV 1 line transformed by SV40 (COS-7); human embryonic kidney line (293 or 293 cells as described, e.g., in Graham et al., J Gen Viral. 36:59 (1977); baby hamster kidney cells (BHK); mouse sertoli cells (TM4 cells as described, e.g., in Mather, Biol. Reprod. 23:243-251 (1980); monkey kidney cells (CV 1); African green monkey kidney cells (VER0-76); human cervical carcinoma cells (HELA); canine kidney cells (MOCK; buffalo rat liver cells (BRL 3A); human lung cells (W138); human liver cells (Hep 02); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFK CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B.K.C. Lo, ed., Humana Press, Totowa, N.J.), pp. 255-268 (2003).

C. Assays

Anti-PD-L1 idiotypic antibodies provided herein may be identified, screened for, or characterized for their physical/chemical properties and/or biological activities by various assays known in the art.

i. Binding Assays and Other Assays

In one aspect, an antibody of the invention is tested for its antigen binding activity, e.g., by known methods such as ELISA, Western blot, etc. Binding affinity can be measured by common methods known in the art. In one embodiment, the $K_D$ of an antibody is measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol. Biol* 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the $K_D$ is measured by using surface-plasmon resonance assays using a BIACORE®-2000 or a BIACORE®-3000 instrument (BIAcore, Inc., Piscataway, N.J.) at 25° C. with immobilized antigen CM5 chips at 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (0.2 µM) before injection at a flow rate of 5 µL/minute to achieve approximately 10 response units (RU) of the coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 10™ surfactant (PBST) at 25° C. at a flow rate of approximately 25 µL/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

In another aspect, competition assays may be used to identify another anti-idiotypic antibody that competes for binding of an anti-PD-L1 antibody with any of anti-PD-L1 idiotypic antibodies described herein. In certain embodiments, such a competing antibody binds to the same epitope (e.g., a linear or a conformational epitope) of an anti-PD-L1 antibody. Detailed exemplary methods for mapping an epitope to which an antibody binds are provided in Morris (1996) "Epitope Mapping Protocols," in Afethods in Afolecular Biology vol. Humana Press, Totowa, N.J.).

In an exemplary competition assay, immobilized anti-PD-L1 antibody is incubated in a solution comprising a first labeled antibody (e.g., a first labeled anti-PD-L1 idiotypic antibody) that binds to the anti-PD-L1 antibody, respectively and a second unlabeled antibody (e.g., a second unlabeled anti-PD-L1 idiotypic antibody) that is being tested for its ability to compete with the first antibody for binding to the anti-PD-L1 antibody. The second antibody may be present in a hybridoma supernatant. As a control, immobilized anti-PD-L1 antibody is incubated in a solution comprising the first labeled antibody but not the second unlabeled antibody. After incubation under conditions permissive for binding of the first antibody to the anti-PD-L1 antibody, excess unbound antibody is removed, and the amount of label associated with immobilized anti-PD-L1 antibody is measured. If the amount of label associated with immobilized anti-PD-L1 antibody is substantially reduced in the test sample relative to the control sample, then that indicates that the second antibody is competing with the first antibody for binding to anti-PD-L1 antibody. See Harlow and Lane (1988) Antibodies: A Laboratory A1anual ch. 14 (Cold Spring Harbor Laboratory, Cold Spring Harbor, N.Y.). Competition assays can also be performed in a manner as described above with FACS using cells transfected with anti-PD-L1 antibody and expressed on the cell surface. Additionally, ELISA with anti-PD-L1 antibody can also be used in a competition assay.

In another aspect, gel shift assays may be used to identify an interaction between an anti-idiotypic antibody of the invention and a target antibody, such as an anti-PD-L1 antibody.

In an exemplary gel shift assay, an anti-PD-L1 antibody is pre-incubated with an anti-idiotypic antibody. The pre-incubated anti-PD-L1 antibody and control anti-PD-L1 antibodies that have not been pre-incubated with an anti-idiotypic antibody are subjected to gel electrophoresis and probed secondary antibodies (e.g., IgG and Ig kappa secondary antibodies for a IgG/Ig kappa anti-PD-L1 antibody). The mobility of the pre-incubated anti-PD-L1 antibody and the control anti-PD-L1 antibody are compared, wherein a difference in the mobility of the pre-incubated anti-PD-L1 antibody and the control anti-PD-L1 antibody indicates an interaction between the anti-PD-L1 antibody and the anti-idiotypic antibody.

D. Methods of Using Anti-Idiotypic Antibodies i. Methods of Use

In certain embodiments, any of the anti-idiotypic antibodies, or compositions comprising such antibodies as provided herein are useful for detecting the presence of anti-PD-L1 antibodies in a biological sample. In certain embodiments any of the anti-PD-L1 idiotypic antibodies or compositions comprising such antibodies as provided herein are useful to quantitate anti-PD-L1 antibody in a sample. In certain embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain the antibody of interest. In various embodiments, the sample is a body sample from any animal. In various embodiments, the sample is a sample from a human.

In certain embodiments any of the anti-idiotypic antibodies, or compositions comprising such antibodies, as provided herein, are useful for detecting the presence of anti-PD-L1 in an immunoassay without affecting its ability to bind to another molecule (e.g., an antibody that binds to the Fc region of the anti-PD-L1 antibody).

The anti-PD-L1 idiotypic antibodies, or compositions comprising such antibodies, can be used in a variety of different assays, including but not limited to ELISA, bead based immunoassays and Mass Spectrometry.

In some embodiments any of the anti-idiotypic antibodies that bind to an anti-PD-L1 antibody, or compositions comprising such antibodies, as provided herein, are useful for depleting, detecting or differentiating the anti-PD-L1 antibody from a patient sample to reduce its interference in an assay.

In some embodiments, the sample is from a mammal. In some embodiments, the sample is from a human subject, for example, when measuring an antibody such as a humanized antibody in a clinical sample. In some embodiments, the biological sample is from clinical patients or a patient treated with a therapeutic anti-PD-L1 antibody (e.g., atezolizumab). In certain embodiments, the biological sample is serum or plasma. In certain embodiments, the biological sample is serum from a clinical patient. In certain embodiments the biological sample is urine. In certain embodiments, the biological sample is urine from a clinical patient.

In certain embodiments, compositions comprising labeled anti-PD-L1 idiotypic antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, J3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

ii. Methods and Compositions for Detection of Anti-PD-L1 Antibodies

1. ELISA

In some embodiments, the anti-PD-L1 idiotypic antibodies are used in an ELISA assay. The assay described herein is an ELISA that utilizes anti-PD-L1 idiotypic antibodies as capture reagents for an antibody of interest. In the first step of the assay the biological sample suspected of containing or containing the antibody of interest is contacted and incubated with the capture (or coat) antibodies so that the capture antibodies capture or bind to the antibody of interest so that it can be detected in a detection step. The detection step involves use of a detectable antibody, which, when contacted with any of the bound antibody of interest, binds to the antibody of interest, if present. A detection means is used to detect the label on the antibody and hence the presence or amount of antibody of interest present.

In certain embodiments, the assay utilizes the following steps.

First Step

In the first step of the assay herein, the biological sample suspected of containing or containing the antibody of interest as defined herein is contacted and incubated with the immobilized capture (or coat) reagents, which are anti-idiotypic antibodies directed against the antibody of interest. In some embodiments, these anti-idiotypic antibodies are monoclonal antibodies, and may be from any species. In some embodiments, these anti-idiotypic antibodies are rodent antibodies, in further embodiments murine or rat, and in further embodiments murine antibodies.

In various embodiments, the anti-idiotypic is any anti-idiotypic antibody disclosed herein. In certain embodiments, the anti-idiotypic antibody is an antibody comprising three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 35; (b) HVR-H2 comprises the amino acid sequence of SEQ ID NO: 36; (c) HVR-H3 comprises the amino acid sequence of SEQ ID NO: 34; (d) HVR-L1 comprises the amino acid sequence of SEQ ID NO: 14; (e) HVR-L2 comprises the amino acid sequence of SEQ ID NO: 15 and (f) HVR-L3 comprises the amino acid sequence of SEQ ID NO: 16. In some embodiments, the anti-idiotypic antibody comprises the heavy chain variable region sequence of SEQ ID NO: 54 and the light chain variable region sequence of SEQ ID NO: 53.

According to another embodiment, the anti-idiotypic antibody is an antibody comprising three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 43; (b) HVR-H2 comprises the amino acid sequence of SEQ ID NO: 44; (c) HVR-H3 comprises the amino acid sequence of SEQ ID NO: 42; (d) HVR-L1 comprises the amino acid sequence of SEQ ID NO: 20; (e) HVR-L2 comprises the amino acid sequence of SEQ ID NO: 21 and (f) HVR-L3 comprises the amino acid sequence of SEQ ID NO: 22. In some embodiments, the anti-idiotypic antibody comprises the heavy chain variable region sequence of SEQ ID NO: 56 and the light chain variable region sequence of SEQ ID NO: 55.

According to another embodiment, the anti-idiotypic antibody is an antibody comprising three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 51; (b) HVR-H2 comprises the amino acid sequence of SEQ ID NO: 52; (c) HVR-H3 comprises the amino acid sequence of SEQ ID NO: 50; (d) HVR-L1 comprises the amino acid sequence of SEQ ID NO: 26; (e) HVR-L2 comprises the amino acid sequence of SEQ ID NO: 27 and (f) HVR-L3 comprises the amino acid sequence of SEQ ID NO: 28. In some embodiments, the anti-idiotypic antibody comprises the heavy chain variable region sequence of SEQ ID NO: 58 and the light chain variable region sequence of SEQ ID NO: 57.

Immobilization conventionally is accomplished by insolubilizing the capture reagents either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al.; J. Immunol. Methods, 57:87-98 (1983)), or afterward, e.g., by immunoprecipitation. In some embodiments, the capture antibody is conjugated to biotin and is bound to a streptavidin coated surface. In other embodiments, the capture antibody is conjugated to a protein tag, such as a His tag or GST, and is bound to a suitable surface, e.g., a nickel or copper coated surface, or a glutathione coated surface.

The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In some embodiments, the immobilized capture reagents are coated on a microtiter plate. In some embodiments, the solid phase used is a multi-well microtiter plate that can be used to analyze several samples at one time, for example, a MICROTEST™ or MAXISORP™ 96-well ELISA plate such as that sold as NUNC MAXISORB™ or IMMULONT™.

The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature.

Commonly used cross-linking agents for attaching the capture reagents to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

If 96-well plates are utilized, they may be coated with the mixture of capture reagents typically diluted in a buffer such as 0.05 M sodium carbonate by incubation for at least about 10 hours. In some embodiments, incubation is at least overnight, at temperatures of about 4-20° C., or about 4-8° C., and at a pH of about 8-12, about 9-10, or about 9.6. If shorter coating times (1-2 hours) are desired, one can use 96-well plates with nitrocellulose filter bottoms (Millipore MULTISCREEN™) or coat at 37° C. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, or about 1.5 to 3 hours.

After coating and blocking, the standard (purified antibody of interest) or the biological sample to be analyzed, appropriately diluted, is added to the immobilized phase. In certain embodiments the dilution rate is about 5-15%, or about 10%, by volume. Buffers that may be used for dilution for this purpose include (a) phosphate-buffered saline (PBS) containing 0.5% BSA, 0.05% TWEEN 20™ detergent (P20), 0.05% PROCLIN™ 300 antibiotic, 5 mM EDTA, 0.25% 3-((3-cholamidopropyl) dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN™ 300, pH 7; (c) PBS containing 0.5% BSA, 0.05% P20, 0.05% PROCLIN™ 300, 5 mM EDTA, and 0.35 M NaCl, pH 6.35; (d) PBS containing 0.5% BSA, 0.05% P20, 0.05% PROCLIN™ 300, 5 mM EDTA, 0.2% beta-gamma globulin, and 0.35 M NaCl; and (e) PBS containing 0.5% BSA, 0.05% P20, 0.05% PROCLIN™ 300, 5 mM EDTA, 0.25% CHAPS, and 0.35 M NaCl. PROCLIN™ 300 acts as a preservative, and TWEEN 20™ acts as a detergent to eliminate non-specific binding.

The amount of capture reagents employed is sufficiently large to give a good signal in comparison with the standards, but not in molar excess compared to the maximum expected level of antibody of interest in the sample. In certain embodiments, the amount of biological sample added is such that the immobilized capture reagents are in molar excess of the maximum molar concentration of free antibody of interest anticipated in the biological sample after appropriate dilution of the sample. This anticipated level depends mainly on any known correlation between the concentration levels of the free antibody of interest in the particular biological sample being analyzed with the clinical condition of the patient. Thus, for example, an adult patient may have a maximum expected concentration of free antibody of interest in his/her serum that is quite high, whereas a child will be expected to have a lower level of free antibody of interest in his/her serum based on the doses given.

The concentration of the capture reagents may be determined by the concentration range of interest of the antibody of interest, taking any necessary dilution of the biological sample into account. The final concentration of the capture reagents may also be determined empirically to maximize the sensitivity of the assay over the range of interest. Generally, the molar excess is suitably less than about ten-fold of the maximum expected molar concentration of antibody of interest in the biological sample after any appropriate dilution of the sample.

The conditions for incubation of sample and immobilized capture reagent are selected to maximize sensitivity of the assay and to minimize dissociation, and to ensure that any antibody of interest present in the sample binds to the immobilized capture reagent. The incubation is accomplished at fairly constant temperatures, ranging from about 0° C. to about 40° C., for example at or about room temperature. The time for incubation is generally no greater than about 10 hours. In various embodiments, the incubation time is from about 0.5 to 3 hours, or from about 1.5-3 hours at or about room temperature to maximize binding of the antibody of interest to the capture reagents. The duration of incubation may be longer if a protease inhibitor is added to prevent proteases in the biological fluid from degrading the antibody of interest.

At this stage, the pH of the incubation mixture will ordinarily be in the range of about 4-9.5, or in the range of about 6-9, or about 7 to 8. The pH of the incubation buffer is chosen to maintain a significant level of specific binding of the capture reagents to the antibody of interest being captured. Various buffers may be employed to achieve and maintain the desired pH during this step, including borate, phosphate, carbonate, TRIS-HC1 or TRIS-phosphate, acetate, barbital, and the like. The particular buffer employed is not critical to the invention, but in individual assays one buffer may be preferred over another.

Optional Second Step

In an optional second step of the assay method, the biological sample is separated (for example by washing) from the immobilized capture reagents to remove uncaptured antibody of interest. The solution used for washing is generally a buffer ("washing buffer") with a pH determined using the considerations and buffers described above for the incubation step, with a pH range of about 6-9. The washing may be done three or more times. The temperature of washing is generally from refrigerator to moderate temperatures, with a constant temperature maintained during the assay period, typically from about 0-40° C., or about 4-30° C. For example, the wash buffer can be placed in ice at 4° C. in a reservoir before the washing, and a plate washer can be utilized for this step. A cross-linking agent or other suitable agent may also be added at this stage to allow the now-bound antibody of interest to be covalently attached to the capture reagents if there is any concern that the captured antibody of interest may dissociate to some extent in the subsequent steps.

Third Step

In the next step, the immobilized capture reagents with any bound antibody of interest present are contacted with detectable antibody at a temperature of about 20-40° C., or about 36-38° C., with the exact temperature and time for contacting the two being dependent primarily on the detection means employed. For example, when 4-methylumbelliferyl-β-galactoside (MUG), streptavidin-HRP, or streptavidin-β-galactosidase is used as the means for detection, the contacting may be carried out overnight (e.g., about 15-17 hours or more) to amplify the signal to the maximum. While the detectable antibody may be a polyclonal or monoclonal antibody, preferably it is a monoclonal antibody, to reduce background noise. In some embodiments, the same anti-idiotypic antibody is used for coat and detection in the assay. In other embodiments, different anti-idiotypic antibodies can be used for coat and detection which are selected so that the background noise is minimized.

In some embodiments, the detectable antibody is an antibody from a non-human species that binds to human antibodies. In some embodiments, the detectable antibody is an anti-huIgG Fc antibody. In some embodiments, the detectable antibody is a mouse anti-huIgG Feγ antibody. In some embodiments, the detectable antibody is directly detectable. In certain embodiments, the detectable antibody is biotinylated. In such cases, the detection means for the biotinylated label may be avidin or streptavidin-HRP, and the readout of the detection means may be fluorimetric or colorimetric. In some embodiments, the antibody is conjugated to HRP, and the detection means is colorimetric.

A molar excess of detectable antibody with respect to the maximum concentration of free antibody of interest expected (as described above) is added to the plate after it is washed. This antibody (which is directly or indirectly detectable) is a monoclonal antibody, although any antibody can be employed. The affinity of the detectable antibody must be sufficiently high that small amounts of the free antibody of interest can be detected, but not so high that it causes the antibody of interest to be pulled from the capture reagents.

Fourth Step

In the last step of the assay method, the level of any free antibody of interest from the sample that is now bound to the capture reagents is measured using a detection means for the detectable antibody. If the biological sample is from a clinical patient, the measuring step comprises comparing the reaction that occurs as a result of the above three steps with a standard curve to determine the level of antibody of interest compared to the known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free antibody of interest to the anti-idiotypic antibodies.

Examples of suitable labels are those numerous labels known for use in immunoassay, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, HRP, alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144:945 (1962); David et al., Biochemistry, 13:1014-1021 (1974); Pain et al., J. Immunol. Methods, 40:219-230 (1981); and Nygren, J. Histochem. and Cytochem., 30:407-412 (1982).

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Suitable commercially available labeled antibodies may also be used.

Following the addition of last labeled antibody, the amount of bound antibody is determined by removing excess unbound labeled antibody through washing and then measuring the amount of the attached label using a detection method appropriate to the label, and correlating the measured amount with the amount of the antibody of interest in the biological sample. For example, in the case of enzymes, the amount of color developed and measured will be a direct measurement of the amount of the antibody of interest present. Specifically, if HRP is the label, the color may be detected using the substrate TMD, using a 450 nm read wavelength and a 620 or 630 nm reference wavelength.

In one example, after an enzyme-labeled second antibody directed against the first unlabeled antibody is washed from the immobilized phase, color or chemiluminescence is developed and measured by incubating the immobilized capture reagent with a substrate of the enzyme. Then the concentration of the antibody of interest is calculated by comparing with the color or chemiluminescence generated by the standard antibody of interest run in parallel.

2. Mass Spectrometry

In some embodiments, the anti-PD-L1 idiotypic antibodies are used in a mass spectrometry assay for anti-PD-L1 antibodies. The assays described herein utilize anti-PD-L1 idiotypic antibodies for immunoaffinity capture of anti-PD-L1 antibodies from a biological sample. The sample may be further processed using a separation technique, such as chromatography, prior to quantification of the anti-PD-L1 antibodies by mass spectroscopy. In some embodiments, characteristic peptide fragments are produced by proteolysis, and the chosen signature peptides are measured as surrogate analytes for the anti-PD-L1 antibodies. In certain embodiments, the surrogate peptides are quantified using HPLC with detection by tandem mass spectroscopy (MS/MS).

a. Processing Biological Samples

An anti-PD-L1 antibody is administered to a mammal, such as a human, or contacted with a biological source selected from a tissue, cell culture, plasma or serum. Analysis from serum and plasma samples is known to be problematic due to their high proteomic background, i.e. many proteins and other analytes. After a certain period of time, ranging from minutes, hours, days after administration, a biological sample comprising the anti-PD-L1 antibody, or fragment thereof is collected. The biological sample may be collected by any means, including withdrawing a fluid by syringe or cannula. The biological sample may be blood or blood products such as serum, plasma or the like or other body fluid containing the antibody of interest.

The biological samples are processed to form analysis samples by conventional procedures including: formulating, immobilizing, centrifugation, isolating, digesting, inducing or preventing blood cell clotting, hydrolyzing, or purifying. Processing biological samples serves to remove impurities and reduce sample heterogeneity which may hinder separation of the sample constituents, or obscure data collection or analysis. Alternatively, or in addition to, processing simplifies sample handling, preserves from degradation, minimizes sample volume, or selects for the sample constituents (analytes) of interest in the mass spectrometric analysis. Alternatively, or in addition to, processing converts biological samples into metabolites, fragments, or derivatives which are of interest in determining drug metabolism or pharmacokinetic effects.

b. Capturing Processed Analysis Samples

The antibody is captured on immune-affinity beads where the beads have an immobilized anti-idiotypic antibody specific for the administered anti-PD-L1 antibody. In various embodiments, the anti-idiotypic is any anti-idiotypic antibody disclosed herein. The anti-idiotypic antibody specific for the administered anti-PD-L1 antibody may be conjugated to the immunoaffinity beads using any suitable method known in the art. In some embodiments, the anti-idiotypic specific for the administered anti-PD-L1 antibody is biotinylated and bound to streptavidin coated paramagnetic beads through strong biotin-streptavidin interaction ($K_D=10^{-15}$ M). Rationales for using streptavidin coated paramagnetic beads include: (i) the strong streptavidin-biotin interaction ($K_D=10^{-15}$ M), (ii) the immobilized streptavidin/biotinylated analyte is a proven method, (iii) the high binding capacity (sufficient material for intact proteins), (iv) low non-specific binding, (v) elution of sample with mass spectrometry-compatible solvents, (vi) good sample recovery from beads, and (vii) ease of use and amenable for automation.

The immune-affinity bead may comprise a porous polymer monolith and may be configured in a flow-through channel in fluid communication with a collection reservoir. The beads may be contained in a flow-through vessel, such as a column or funnel wherein the sample from the biological source is introduced at one end or orifice, and a sample is eluted from another end or orifice. The immune-affinity beads may be distributed in a plurality of flow-through vessels, each in communication with a separate collection reservoir. The vessels and reservoirs may be configured in a 96 microtitre well format of 12×8 columns and rows, or a 384 microtitre well format of 24×16 columns and rows for purposes of automation and reproducibility of results.

Plasma or serum samples from the mammal (biological source) that received the anti-PD-L1 antibody are applied to the beads by manual pipetting or automated robotic dispensing.

The beads may be configured in a well or other vessel, or configured in a column, or other flow-through device where the sample is introduced at one end or orifice, and wash effluent or eluted sample is eluted from another end or orifice. Sample constituents specific for the bead bound anti-idiotypic antibody are allowed to bind. The beads are washed to rinse off non-specific proteins and other non-specific sample constituents. Bound antibodies may be deglycosylated on the beads, e.g. with PNGaseF. The bound sample constituents may be eluted into a sample plate, with segregated receiving vessels or wells. The eluted samples may then be addressed by manual pipetting or by robotic transfer and separated by reverse phase chromatography and the separated sample constituents are analyzed by mass spectrometry.

In some embodiments, the biological sample may be digested with a protease. Characteristic peptide fragments are produced by proteolysis, and the chosen signature peptides are measured as surrogate analytes for the anti-PD-L1 antibodies. In an exemplary embodiment, the biological sample may be digested with trypsin digestion. For trypsin digestion, samples may be reduced with DTT, S-carboxymethylated with sodium iodoacetate, and then digested with trypsin. Digested samples may be analyzed by a separation method, for example, reverse phase HPLC, e.g. Nucleosil C18 column; size-exclusion chromatography (SEC), e.g. TSK 3000SWxL column; or boronate affinity chromatography using a TSK Boronate column.

c. Separation of Sample Constituents

To form the analysis sample, the biological sample may be applied to a separation media to effect separation of more than one sample constituent. Separation methods include affinity, chromatography, and electrophoresis methods. Affinity methods include affinity chromatography, adsorption, and immobilized affinity matrices. Chromatography methods include HPLC, hydrophobic interaction (HIC), anion exchange, cation exchange, reverse-phase, normal phase, ion-pair reverse-phase, thin-layer, capillary flow, and size-exclusion. Electrophoretic methods include single dimensional, slab gel, capillary, polyacrylamide, denaturing, native, free solution, paper, 2-dimensional, isoelectric focusing, and gradient voltage. Other separation methods include: dialysis, centrifugation, sedimentation, floatation, precipitation, immunoprecipitation, and gel filtration.

Separation methods may effect separation of the constituents of the biological sample by one or more physico-chemical properties including, but not limited to, elution time, hydrophobicity, hydrophilicity, migration time, rate, velocity, chromatographic retention time, solubility, molecular volume or size, net charge, charge state, ionic charge, isoelectric point, dissociation constant (pKa), antibody affinity, electrophoretic mobility, ionization potential, dipole moment, hydrogen-bonding capability, and ion mobility in gas phase.

Low rate of flow by capillary flow infusion into the mass spectrometry inlet device facilitates sensitivity of mass detection, allowing for lower concentration analytes and higher molecular weight species such as intact proteins and antibodies to be detected and characterized.

d. Mass Spectrometry of Separated Sample Constituents

Preparation of samples for mass spectrometric analysis can be conducted generally according to known techniques. See: "Modem Protein Chemistry: Practical Aspects", Howard, G. C. and Brown, W. E., Eds. (2002) CRC Press, Boca Raton, Fla.

The methods of the invention are appropriate for the analysis of antibody mixtures derived from biological samples where different chemical constituents of the mixture are first isolated, separated, or partially separated by one or more processes including affinity or chromatography which cause the constituents to elute sequentially or in a batch wise manner, or to be directly detected by mass spectrometry. Various structural features and properties of antibodies can be elucidated from mass spectrometry analysis including: fragmentation, deamidation, glycation, oxidation, partial sequence information, e.g. N-terminal and C-terminal, dimer and aggregation states. One or more chemical constituents in the biological sample can be characterized in a highly specific manner by measurement of its accurate mass since the administered anti-PD-L1 antibody is of known sequence, structure, and molecular weight.

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and atmospheric pressure chemical ionization (APCI) and Matrix Assisted Laser Desorption Ionization (MALDI). ESI and MALDI are the two most commonly employed methods to ionize proteins for mass spectrometric analysis. ESI and APCI are the most commonly used ion source techniques for analysis of small molecules by LC/MS (Lee, M. "LC/MS Applications in Drug Development" (2002) J. Wiley & Sons, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing multiple reactive moieties at different sites on a substrate surface, throughput may be increased.

In functional systems, the mass spectrometer will accurately measure the mass of a chemical species of interest to within 20 ppm of its exact or calculated mass, and typically within 5 ppm or less of its exact or calculated mass. Commercially available mass analyzers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

Analytical variability may be corrected for by the use of an internal standard (IS) having physicochemical properties similar to that of the target analyte. (Mesmin et al. (2011) Bioanalysis 3: 477-480). In some embodiments, where signature peptides are measured as surrogate analytes for the anti-PD-L1 antibodies, stable isotope labled (SIL) peptides corresponding to the signature peptides may be used as internal standards. (Hagman et al. (2008) Anal. Chem. 80: 1290-1296; Mesmin et al. (2010) Rapid Commun. Mass Spectrom. 24: 2875-2884).

3. Electrospray Ionization Mass Spectrometry (ESI)

Higher sensitivity is achieved at lower flow rates due to increased analyte ionization efficiency (Gale et al (1993) Rapid Commun. Mass Spectrom. 7:1017). Thus by performing electrospray injection of a sample-containing fluid at flow rates in the nanoliter per minute range provides for accurate quantitation after proper calibration, and the high sensitivity for an analyte contained within the fluid when combined with mass spectrometry. Systems and devices including a miniaturized and consolidated micro-column and micro-column array having affinity chromatographic adsorbents, which offer high selectivity and sensitivity, and accurate qualitative analysis as front ends to MS have been reported (U.S. Pat. Nos. 6,811,689; 6,020,208; 6,579,719).

Masses of relatively high molecular weight compounds such as antibodies can be detected at mass-to-charge ratios (m/z) that are easily determined by most mass spectrometers (typical m/z ranges of up to 2000 to 3000). Electrospray ionization mass spectrometry ESI-MS, in particular, is suited for charged, polar or basic compounds and for analyzing multiply charged compounds with excellent detection limits. ESI thus allows detection and characterization of large biomolecules, such as antibodies and antibody-drug conjugates with molecular weight (MW) of 150,000 or higher. With high-mass ions, a series of multiply charged molecular ions are typically observed. The molecular weight for positive ions is determined by multiplying the measured m/z ratio with the number of charges (n) minus the mass of the cation (C+) times the number of charges (n) on that ion.

The ESI method allows the presence or absence of fragmentation to be controlled by controlling the interface lens potentials. Electrospray ionization (ESI) is compatible with liquid separation methods (front end), as well as mass spectrometric detection methods (back end) ("Electrospray Ionization Mass Spectrometry: Fundamentals, Instrumentation, and Applications", Cole, R. B., Ed. (1997) Wiley, New York.

ESI-MS data may be acquired by averaging a number of scans together and smoothing the data to provide good peak intensity and shape. For low-mass compounds, the most abundant peaks observed are often the [M+H]+ ions in the positive-ion mode and [M−H]− in the negative ion mode. Doubly and triply charged ions as well as dimers may also be observed. Doubly charged positive ions will be observed at a mass (MW+2C+)/2 where MW is the molecular weight and C+ is the ionizing cation, such as $H^+$, $Na^+$, or $NH4^+$. Except for the very low mass compounds, the detected ions will be multiply charged. Due to the soft (low ionizing potential) conditions of ESI, typically only molecular ions are observed. ESI spectra may have several molecular ion peaks that differ in the mass to charge ratio due to various numbers of charges the ion possesses.

A dilute solution of a sample, e.g. ADC or other biomolecule may be slowly pumped through a hypodermic needle for ESI-MS analysis. The sample may be introduced via flow injection or LC/MS. Typical flow rates range from less than 1 microliter (µl) per minute up to about one milliliter (ml) per minute. ESI is particularly suited for large biological molecules that are otherwise difficult to vaporize or ionize. The needle is held at a high voltage and the strong electric field at the end of the needle charges the nebulized solution and creates charged droplets. The charged droplets evaporate water to ultimately yield molecular ions that travel into the vacuum chamber through a small orifice. During the process of solvent evaporation, the non-covalently bound complex is transferred from solution to gas phase. (Hu et al (1994)).

Gentle desolvation conditions are generally required to maintain the intact gas-phase complex. The orifice may be heated to ensure that the ions are completely desolvated. Some MS systems may employ a counter-flowed heated gas. Charged droplets are emitted from a hypodermic needle and shrink as they evaporate solvent before entering a vacuum chamber. Heat and gas flows may be used to aid desolvation. The amount of sample required for ESI measurements may be reduced by reducing the fluid flow by use of small capillary electrospray emitter, tips, a process known as nanoelectrospray. Nanoelectrospray methods can produce a constant signal for about I 0-30 minutes for a 1 µl sample. The low flow has been shown to increase the ion efficiency and reduce ion suppression. Nanoelectrospray methods are frequently used for MS/MS protein studies (Komer et al (1996) J. Am. Soc. Mass Spectrom. 7:150-156; Mann, M. and Wilm, M. (1996) Anal. Chem. 68:1-8.

ESI of proteins produce multiply charged ions with the number of charges tending to increase as the molecular weight increases. The number of charges on a given ionic species may be determined by methods such as: (i) comparing two charge states that differ by one charge and solving simultaneous equations; (ii) looking for species that have the same charge but different adduct masses; and (iii) examining the mass-to-charge ratios for resolved isotopic clusters. The methods of ESI and ESI-MS and parameters needed to conduct these methods are well known in the art. The gentleness of the electrospray ionization process allows intact antibody conjugates to be directly detected by mass spectrometry.

In one embodiment, a Q1 mass spectrum of the protein, antibody, antibody fragment or antibody-conjugates (large molecules) is run as part of the method. A suitable quality Q1 mass spectrum of a large molecule can be obtained. Since there is potential for the protein envelope to shift, all the solvents used for chromatography are made fresh and acid is added to the elution solvent to position the spectrum envelop in the observed range. For proteins of greater than 100,000 mass units, an acid such as formic acid can be used at about 0.1% (volume) in the elution solvents, for example, both solvent A (water) and B (acetonitrile). A stronger acid can be used, such as trifluoroacetic acid (TFA), at 0.05% (volume) TFA for both A and B solvents for proteins with less than 100,000 mass units. As the amount of formic acid is decreased, the intact glycosylated antibody, trastuzumab, picks up more charge, shifting the envelope further to the left and into the observed range of m/z (1800-3000 m/z). As the declustering potential (DP) voltage is increased from about 30-120V to about 70-190V, the charge on the antibody increases even further. Thus voltage applied, solvent composition, and ion pairing agents are factors to consider and adjust. The declustering potential (DP) may be increased (ramped) to acquire enough resolution to select the best charge ion range. Linearity may be obtained over a wide range of m/z. Deglycosylation of the antibody assists quantitation of intact antibody or heavy chain, fragments or ADC. Glycosylation contributes to lower ionization efficiency and thus reduced sensitivity. When quantitating antibody or antibody fragment conjugates, deglycosylation of the antibody may reduce the heterogeneity of the mass spectrum, increase sensitivity and thus simplifying the analysis.

Deconvolution tables are used to determine the exact mass to charge ratio (m/z) for each species to quantitated. Deconvolution software applications such as Analyst™ QS (Applied Biosystems, Foster City, Calif.) are commercially available and/or provided with mass spectrometers. Deconvolution software generally provides the user with a table of deconvoluted masses as well as a sub-table of m/z ions used to calculate these masses.

iii. M-protein Detection

Multiple myeloma (MM) is a cancer of plasma cells in the bone marrow. Multiple myeloma causes high levels of proteins in the blood, urine, and organs, including but not limited to M-protein and other immunoglobulins (antibodies) and beta-2-microglobulin. M-protein, short for monoclonal protein, also known as paraprotein, is produced by the myeloma plasma cells and can be found in the blood or urine of almost all patients with multiple myeloma.

Immunomodulatory drugs such as lenalidomide (Revlimid®) have emerged as important options for the treatment of myeloma in newly diagnosed patients, in patients with advanced disease who have failed chemotherapy or transplantation, and in patients with relapsed or refractory multiple myeloma. Another potent immunomodulatory agent is 4-(amino)-2-(2,6-dioxo(3-piperidyl))-isoindoline-1,3-dione (pomalidomide, Actimid®). In some cases, such agents are used in combination with standard chemotherapy agents. For example, lenalidomide in combination with dexamethasone was recently approved for the treatment of patients with multiple myeloma who have received at least one prior therapy. Pomalidomide may also be administered in combination with dexamethasone. Atezolizumab (Tecentriq®), in combination with other treatments is being tested in multiple clinical trials as a therapy for multiple myeloma.

The International Myeloma Working Group (IMWG) has established criteria for clinical response to treatment in MM, which include changes in serum/urine M-protein levels by serum protein electrophoresis (SPE), and immunofixation electrophoresis (IFE), percentage of bone marrow plasma cells, and free light chain (FLC) ratios. For a patient to be classified as having a complete response (CR) by IMWG criteria, the serum and urine must be negative for M-protein as determined by IFE and SPE, and bone marrow plasma cells must be <5%. The treatment of MM is evolving with the introduction of therapeutic monoclonal antibodies. Since SPE and IFE are used to quantify and characterize the clonal nature of immunoglobulins, respectively, these assays are subject to interference by monoclonal antibodies used during therapy. The anti-idiotypic antibodies of this invention can be used to shift anti-PD-L1 antibodies in a biological sample during clinical assays for detecting M protein.

Immunofixation Electrophoresis (IFE)

Immunofixation electrophoresis (IFE) is known in the art and is a two stage procedure using agarose gel protein electrophoresis in the first stage and immunoprecipitation in the second. The specimen may be any biological sample. In a preferred embodiment, the specimen is serum, urine or cerebral spinal fluid. In one embodiment, IFE comprises the steps of: (a) separating proteins by electrophoresis on an agarose gel; (b) performing immunofixation (immunoprecipitation) of the electrophoresed proteins, wherein the appropriate electrophoretic migration tracks are overlaid with individual antisera, the antisera diffuse into the gel and precipitate the corresponding antigens when present and the proteins in the reference track are fixed with a fixative; (c) removing the unprecipitated, soluble proteins from the gel by blotting and washing, wherein precipitin of the antigen-antibody complex is trapped within the gel matrix; and (d) visualizing the precipitated proteins by staining. In some embodiments, the immunofixation electrophoresis process comprises; (a) applying a sample to at least two application areas on an electrophoretic gel; (b) electrophoresing the gel; (c) aligning a template onto the electrophoresed gel, the template having a template slot corresponding to each electrophoresed area; (d) applying a composition capable of fixing proteins in situ to at least one template slot and applying an antiserum capable of reacting with one protein to at least one of the remaining template slots; (e) incubating the resultant product of the step (d); (f) removing the template from the incubated, electrophoresed gel; (g) washing the incubated, electrophoresed gel of step (f); (h) drying the washed gel of step (g); (i) staining the dried gel of step (h); (j) destaining the stained gel of step (i); (k) drying the destained gel of step (j); and (l) analyzing the dried gel of step (k).

In some embodiments, the method is used to detect an anti-PD-L1 antibody in a biological sample. In some embodiments, the method comprises (a) contacting the biological sample with an anti-idiotypic antibody or composition as described herein under a condition to allow binding of the anti-idiotypic antibody to the anti-PD-L1 antibody to form a complex; (b) loading an electrophoresis gel and comparing the migration of proteins in the biological sample that has been contacted with the anti-idiotypic antibody to the biological sample that has not been contacted with the anti-idiotypic antibody by Immunofixation Electrophoresis; wherein a difference in the migration of a band between the sample contacted with the anti-idiotypic antibody and the sample that has not been contacted with the anti-idiotypic antibody indicates the presence of the anti-PD-L1 antibody in the biological sample.

In some embodiments, the method is used to detect M-protein in a biological sample. In some embodiments, the method comprises (a) contacting the biological sample with an anti-idiotypic antibody or composition as described herein under a condition to allow binding of the anti-idiotypic antibody to the anti-PD-L1 antibody to form a complex; (b) loading an electrophoresis gel and comparing the migration of proteins in the biological sample that has been contacted with the anti-idiotypic antibody to biological sample that has not been contacted with the anti-idiotypic antibody by Immunofixation Electrophoresis. In some embodiments, M-protein is detected if there is no difference between the migration of the bands in the sample that has been contacted with the anti-idiotypic antibody and the sample that has not been contacted with the anti-idiotypic antibody. In some embodiments, M-protein is detected if there is a partial shift in the migration of a band in the sample that has been contacted with the anti-idiotypic antibody and the sample that has not been contacted with the anti-idiotypic antibody. In some embodiments, M-protein is not detected if there is a difference between the migration of the bands in the sample that has been contacted with the anti-idiotypic antibody and the sample that has not been contacted with the anti-idiotypic antibody.

Several companies provide automated options that consolidate one or more of these steps. Assays may be performed according to the instructions provided by the company which commercializes the immunofixation electrophoresis assay. For example, the assays can be performed as described at http://www.ilexmedical.com/files/Sebia%20inserts/IF_Standard_mask_Hydrasis.pdf.

III. KITS

The assay methods of this invention can be provided in the form of a kit. In one embodiment, such a kit comprises an anti-idiotypic antibody or a composition comprising an anti-idiotypic antibody as described herein. In some embodiments, such a kit is a packaged combination including the basic elements of: a capture reagent comprised of an anti-idiotypic antibody against the antibody of interest; a detectable (labeled or unlabeled) antibody that binds to the antibody of interest; and instructions on how to perform the assay method using these reagents. These basic elements are defined hereinabove.

The kit may further comprise a solid support for the capture reagents, which may be provided as a separate element or on which the capture reagents are already immobilized.

Hence, the capture antibodies in the kit may be immobilized on a solid support, or they may be immobilized on such support that is included with the kit or provided separately from the kit. In some embodiments, the capture reagents are coated on or attached to a solid material (for example, a microtiter plate, beads or a comb). The detectable antibodies may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme; where the label is a fluorophore, a dye precursor that provides the detectable chromophore; and where the label is biotin, an avidin such as avidin, streptavidin, or streptavidin conjugated to HRP or β-galactosidase with MUG.

In various embodiments, the anti-idiotypic antibody is one or more of any of the anti-idiotypic antibodies disclosed herein. In some embodiments, the anti-idiotypic antibody is selected from (a) an anti-idiotypic antibody comprising the heavy chain variable region sequence of SEQ ID NO: 54 and the light chain variable region sequence of SEQ ID NO: 53; (b) an anti-idiotypic antibody comprising a heavy chain variable region sequence of SEQ ID NO: 56 and a light chain variable region sequence of SEQ ID NO: 55; (c) an anti-idiotypic antibody comprising a heavy chain variable region sequence of SEQ ID NO: 58 and a light chain variable region sequence of SEQ ID NO: 57 and (d) a combination thereof.

The kit also typically contains the antibody of interest as a standard as well as other additives such as stabilizers, washing and incubation buffers, and the like.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

In various embodiments, a kit comprising an anti-idiotypic antibody as described herein is for use in a method as described herein (e.g., in a method of detecting M-protein). In some embodiments, the kit further comprises an anti-idiotypic antibody coated or attached to a comb for use in a method of detecting M-protein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Generation and Characterization of Anti-idiotypic Antibodies Against Anti-PD-L1 Antibody Atezolizumab Generation of Hybridomas Five Balb/c mice (Charles River Laboratories International, Inc., Wilmington, Mass., USA) were hyperimmunized, in each hind footpad and intraperitoneally at 3-4 day intervals, with anti-PDL1 antibody atezolizumab in an adjuvant containing metabolizable squalene, Tween 80, trehalose 6,6-dimycolate and monophosphoryl lipid A (all components obtained from Sigma Aldrich, USA). After 11 boosts, serum titers were evaluated by standard enzyme-linked immunosorbant assay (ELISA) to identify mice with positive serum titers to the anti-PDL1 antibody. B cells from spleens and popliteal lymph nodes were fused with mouse myeloma cells (X63.Ag8.653 or P3X63Ag.U1; American Type Culture Collection, Manassas, Va., USA) by electrofusion (Hybrimune-Hybridoma Production System; Harvard Apparatus, Inc., Holliston, Mass., USA). After 10-14 days, hybridoma supernatants were harvested and screened for CDR specific antibody production by ELISA.

Antibody Cloning and Sequences

To clone out antibody sequences of hybridoma cells for recombinant antibody production, total RNA isolated from cultured hybridoma cells was used for generating cDNA, the PCR template for antibody variable region amplification. The oligos used for PCR are based on mouse V-gene and J-gene germline sequences. In order to subclone PCR products directly to the mammalian expression vectors, flanking vector sequences were appended in the 5'- and 3'-end of forward and reverse primers respectively. The variable regions of heavy and light chain were amplified separately with pooled germline oligos, PCR products were visualized on DNA gel to confirm a single band at expected size (400 bps for heavy chain and 350 bps for light chain).

Purified heavy and light chain PCR products were subcloned into pRK5P-mouse IgG2a and pRK5P-mouse kappa vector respectively with In-Fusion (Clontech) kit. After transformation of ligation products, several single colonies were picked for DNA sequencing. DNA sequences were aligned to IMGT germline database; clones with consensus sequences were selected and scaled up for protein expression.

To confirm the recombinant antibody sequences, heavy and light chain plasmids were co-transfected transiently into HEK293T cells. Purified recombinant IgGs were characterized and compared binding activity and affinity with IgGs isolated from hybridoma culture.

The amino acid sequences of the heavy and light chain variable domains for monoclonal antibodies 105D11, 43B5 and 48C1 were determined as shown in FIGS. 1 and 2.

Characterization of Anti-idiotypic Antibody Binding to Atezolizumab by BIAcore

Binding affinities of anti-PDL1 anti-ID antibodies were measured by Surface Plasmon Resonance (SPR) using a BIAcore™-T2000 instrument. Anti-idiotypic antibodies were captured by an anti-mouse-Fc antibody coated on CM5 biosensor chips to achieve approximately 200 response units (RU). For kinetics measurements, 500 nM of anti-PDL1 Fab or framework control Fab (YW167B.43) (Genentech, South San Francisco, Calif.) were injected in HBS-P+ buffer (0.1M HEPES, 1.5M NaCl, 0.5% Surfactant P20—GE Life Science) at 25° C. with a flow rate of 30 µl/min. Association rates ($k_a$) and dissociation rates ($k_d$) were calculated using a simple one-to-one Langmuir binding model (BIAcore Evaluation Software version 3.2). The equilibrium dissociation constant ($K_D$) was calculated as the ratio $k_{off}/k_{on}$. See Table 2. See also FIG. 3-5.

TABLE 2

Binding kinetics of anti-idiotypic antibodies to atezolizumab

| Antibody | $k_a$ 1/(1/Ms) | $k_d$ 1/(1/s) | $K_D(M)$ |
|---|---|---|---|
| 105D11 | 2.79E+05 | 4.50E-03 | 1.65E-08 |
| 43B5 | 9.50E+04 | 8.62E-03 | 9.07E-08 |
| 48C1 | 4.21E+05 | 9.77E-04 | 2.31E-09 |

Example 2

Figure 6:
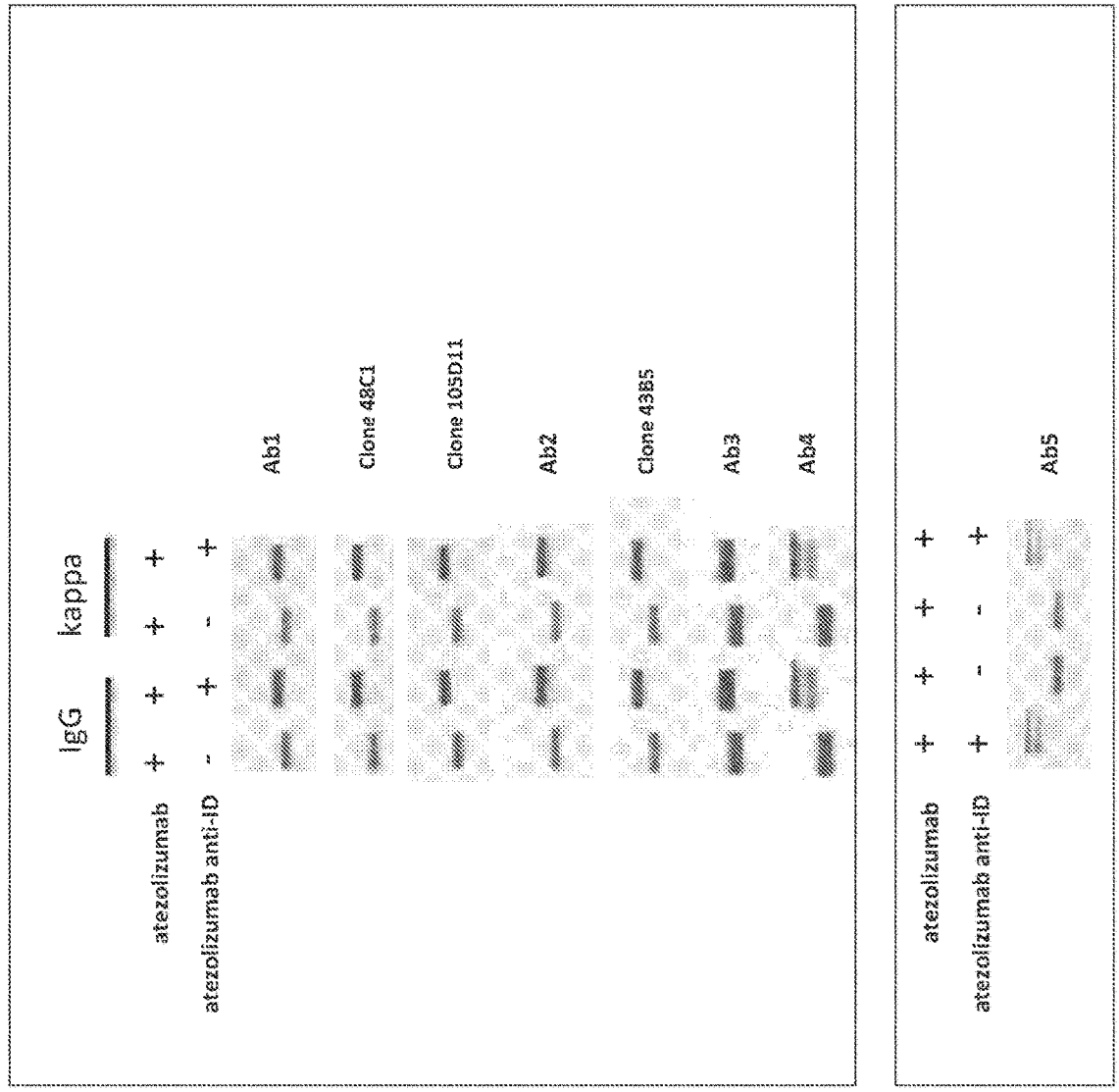
FIG. 6 shows screening of anti-idiotypic antibodies on the Sebia immunofixation electrophoresis (IFE) assay.

Screening of Anti-idiotypic Antibodies for Use in Immunofixation Electrophoresis Assays A screen of anti-idiotypic (anti-ID) antibodies against atezolizumab was conducted on the Sebia IFE platform to identify anti-ID antibodies that bind to atezolizumab and result in a clean 'gel shift' on the Sebia IFE platform. See FIG. 6.

Briefly, samples were set up according to standard laboratory procedures for the handling, storage and preparation of serum for use in gel electrophoresis. The HYDRASYS instrument was set up according to manufacturer's guidelines. Migration protocol and Gel processing set-up was done according to the protocol specified by the manufacturer.

Atezolizumab (1500 µg/mL) was re-suspended in PBS and pre-incubated for 2 hours at room temperature on a shaking platform with the respective anti-ID antibody or sham control (PBS alone). Samples were separated using electrophoresis performed on semi-automatic Hydrasys or Hydrasys 2 using Maxikit Hydragel 41F or 91F (Sebia, Norcross, Ga., USA). Immunofixation (IFE) of the gel was then performed according to the manufacturer's specification using secondary antibodies, such as IgG, Ig kappa, Ig lambda, IgA and/or IgM, as per Sebia IFE protocol. Results illustrate that atezolizumab is detectable on a clinical assay platform, and that the specific complex of atezolizumab plus anti-ID can be separated from atezolizumab alone. Thus, the change in electrophoretic mobility of an IgG/Ig kappa antibody after addition of the anti-atezolizumab (anti-ID) antibody provides evidence of the antibody's identity, namely atezolizumab. See FIG. 6. Based on the data shown in FIG. 6, antibodies 48C1, 105D11 and 43B5 were selected since the complex of atezolizumab with one of these antibodies demonstrated clean gel shift on the Sebia IFE platform.

Figure 8:
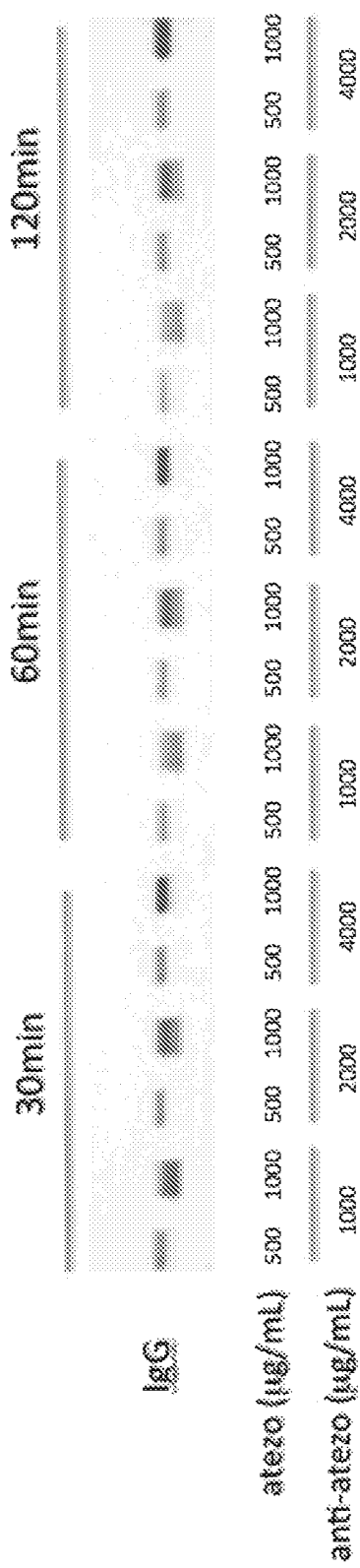
FIG. 8 shows the effect of atezolizumab serum concentration on the ability of anti-idiotypic antibodies to alter the mobility of atezolizumab in the IFE assay.

When the concentration of atezolizumab in the serum is increased, the ability of the anti-ID antibody to change the electrophoretic mobility of atezolizumab depends on the concentration of the anti-ID antibody and the incubation time. See FIG. 8. A complete gel shift of atezolizumab was observed with a 1:1 ratio of atezolizumab:anti-ID antibody when the concentration of atezolizumab in the serum was 500 μg/ml and the incubation time was 2 hours. However, when the concentration of atezolizumab in the serum was increased to 1000 μg/ml, a 1:4 ratio of atezolizumab:anti-ID antibody was required to result in a complete gel shift of atezolizumab. See FIG. 8.

Example 3

Detecting Atezolizumab in the Presence of M Protein Spikes in Serum Samples from Multiple Myeloma Patients Human serum sample from a patient with multiple myeloma was used. The patient's sample showed detectable IgA/Ig kappa M protein spikes in serum after IFE (FIG. 7, panel 1 lane A and lane K). Patient's serum was pre-incubated for 30 minutes to 2 hours in the following conditions: atezolizumab anti-ID antibody 48C1 alone at 1500 μg/ml (FIG. 7 Panel 2), atezolizumab alone spiked in at 1500 μg/ml (FIG. 7, panel 3), and atezolizumab+atezolizumab anti-ID antibody 48C1 at 1500 μg/ml each (FIG. 7, panel 4). Immunofixation (IFE) assays were performed on semi-automatic Hydrasys 2 using Maxikit Hydragel 41F or 91F (Sebia, Norcross, Ga., USA). IFE assays were performed according to the manufacturer's specification. Data were analyzed to determine the effectiveness of the atezolizumab anti-ID antibody to shift the atezolizumab band in IFE assays used routinely for clinical response assessment in multiple myeloma patients.

In FIG. 7, panel 2, the patient serum sample was pre-incubated with atezolizumab anti-ID antibody. Comparison of panel 1 with panel 2 shows that pre-incubation of serum with the atezolizumab anti-ID antibody does not interfere with the results of the patient's detectable M-protein.

In FIG. 7, panel 3, the patient serum sample was pre-incubated with 1500 μg/ml of atezolizumab. Comparison of panel 1 with panel 3, shows the addition of a detectable minor band in panel 3 (arrows lane G and K). This confirms that large biologic drugs, such as atezolizumab which is an IgG/Ig kappa human mAB, are detectable and can interfere with the results of an IFE assay used routinely for clinical response assessment in Multiple Myeloma patients.

In FIG. 7, panel 4, the patient serum sample was pre-incubated with both atezolizumab and atezolizumab anti-idiotype mouse mAB clone #48C1. Comparing panel 3 with panel 4 (FIG. 7) shows that the addition of atezolizumab anti-idiotype mouse monoclonal antibody to the serum sample spiked with atezolizumab, results in a binding complex of the anti-idiotype monoclonal antibody and atezolizumab, thereby resulting in a detectable IgG and Ig kappa shift of the atezolizumab IgG and Ig kappa from a lower to a higher molecular weight on the IFE gel, without disturbing the M protein migration (FIG. 7, panel 4, lane G and K).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Anti-PD-L1 Idiotypic Antibody Amino Acid Sequences

| | HVR Type | SEQ ID NO | HVR L1 | SEQ ID NO | HVR L2 | SEQ ID NO | HVR L3 |
|---|---|---|---|---|---|---|---|
| 105D11 | Contact | 11 | VSYMHWF | 12 | LWIYS TSNLA | 13 | QQRSS YPPT |
| | Chothia | 14 | SASSS VSYMH | 15 | STSNLAS | 16 | QQRSS YPPTF |
| | Kabat | 14 | SASSS VSYMH | 15 | STSNLAS | 16 | QQRSS YPPTF |
| 43B5 | Contact | 17 | SSNIGWL | 18 | GLIYH GTNLE | 19 | VQYAQ FPLT |
| | Chothia | 20 | HASQGI SSNIG | 21 | HGTNLED | 22 | VQYAQ FPLTF |
| | Kabat | 20 | HASQGI SSNIG | 21 | HGTNLED | 22 | VQYAQ FPLTF |
| 48C1 | Contact | 23 | VSYMHWF | 24 | LWIYS TSNLA | 25 | QQRSG YPPT |
| | Chothia | 26 | SASSS VSYMH | 27 | STSNLAS | 28 | QQRSG YPPTF |
| | Kabat | 26 | SASSS VSYMH | 27 | STSNLAS | 28 | QQRSG YPPTF |

| | | SEQ ID NO | HVR H1 | SEQ ID NO | HVR H2 | SEQ ID NO | HVR H3 |
|---|---|---|---|---|---|---|---|
| 105D11 | Contact | 29 | SSYDMS | 30 | WVAYISS GGGSTY | 31 | ARLVYY DYDDA |
| | Chothia | 32 | GFAFSSY | 33 | SSGGGS | 34 | LVYYDY DDAMDY |
| | Kabat | 35 | SYDMS | 36 | YISSGGGST YYPDTVKG | 34 | LVYYDY DDAMDY |
| 43B5 | Contact | 37 | TDYIML | 38 | WIGNINP YYGSTS | 39 | ARWGGN YEGWF |
| | Chothia | 40 | GYSFTDY | 41 | NPYYGS | 42 | WGGNYE GWFAY |
| | Kabat | 43 | DYIML | 44 | NINPYYGST SYNLKFKG | 42 | WGGNYE GWFAY |
| 48C1 | Contact | 45 | SSYDMS | 46 | WVAYISS GGGSTY | 47 | ARTIYY GYDDV |
| | Chothia | 48 | GFAFSSY | 49 | SSGGGS | 50 | TIYYGY DDVMDY |
| | Kabat | 51 | SYDMS | 52 | YISSGGGST YYPDTVKG | 50 | TIYYGY DDVMDY |

| | Light chain variable region | Heavy chain variable region |
|---|---|---|
| 105D11 | SEQ ID NO: 53 | SEQ ID NO: 54 |
| 43B5 | SEQ ID NO: 55 | SEQ ID NO: 56 |
| 48C1 | SEQ ID NO: 57 | SEQ ID NO: 58 |

| | Light chain | Heavy chain |
|---|---|---|
| 105D11 | SEQ ID NO: 59 | SEQ ID NO: 60 |
| 43B5 | SEQ ID NO: 61 | SEQ ID NO: 62 |
| 48C1 | SEQ ID NO: 63 | SEQ ID NO: 64 |

Anti-idiotypic Anti-PD-L1 Antibody 105D11 Light Chain Variable Region Amino Acid Sequence (SEQ ID NO: 53)
DIVLTQSPAIMSASPGEKVTITCSASSSVSYMHWFQQKPGTSPKLWI

YSTSNLASGVPARFSGSGSGTSYSLTISRMEAEDAATYYCQQRSSYP

PTFGGGTRLEIK

Anti-idiotypic Anti-PD-L1 Antibody 105D11 Heavy Chain Variable Region Amino Acid Sequence (SEQ ID NO: 54)
EVQLVETGGGLVKPGGSLKLSCAASGFAFSSYDMSWVRQTPEKRLEW

VAYISSGGGSTYYPDTVKGRFTISRDNAKNTLYLQMSSLKSEDTAMY

YCARLVYYDYDDAMDYWGQGTSVTVSS

Anti-idiotypic Anti-PD-L1 Antibody 43B5 Light Chain Variable Region Amino Acid Sequence (SEQ ID NO: 55)
DIKMTQSPSSMSVSLGDTVSITCHASQGISSNIGWLQQKPGKSFKGL

IYHGTNLEDGVPSRFSGSGSGADYSLTISSLESEDFADYYCVQYAQF

PLTFGAGTKLELK

Anti-idiotypic Anti-PD-L1 Antibody 43B5 Heavy Chain Variable Region Amino Acid Sequence (SEQ ID NO: 56)
EVQLQQSGPELVKPGASVKISCKASGYSFTDYIMLWVKQSHGKSLEW

IGNINPYYGSTSYNLKFKGKATLTVDKSSSTAYMQLNSLTSEDSAVY

YCARWGGNYEGWFAYWGQGTLVTVSA

Anti-idiotypic Anti-PD-L1 Antibody 48C1 Light Chain Variable Region Amino Acid Sequence (SEQ ID NO: 57)
QIVLTQSPAIMSASPGEKVTITCSASSSVSYMHWFQQKPGTSPKLWI

YSTSNLASGVPARFSGSGSGTSYSLTISRMEAEDAATYYCQQRSGYP

PTFGGGTKLEIK

Anti-idiotypic Anti-PD-L1 Antibody 48C1 Heavy Chain Variable Region Amino Acid Sequence (SEQ ID NO: 58)
EVQLVESGGGLVKPGGSLKLSCAASGFAFSSYDMSWVRQTPEKRLEW

VAYISSGGGSTYYPDTVKGRFTISRDNAKNTLYLQMSSLKSEDTAMY

YCARTIYYGYDDVMDYWGQGTSVTVSS

Anti-idiotypic Anti-PD-L1 Antibody 105D11 Light Chain Amino Acid Sequence (SEQ ID NO: 59)
DIVLTQSPAIMSASPGEKVTITCSASSSVSYMHWFQQKPGTSPKLWI

YSTSNLASGVPARFSGSGSGTSYSLTISRMEAEDAATYYCQQRSSYP

PTFGGGTRLEIKRADAAPTVSIFPPSSEQLTSGGASVVCFLNNFYPK

DINVKWKIDGSERQNGVLNSWTDQDSKDSTYSMSSTLTLTKDEYERH

NSYTCEATHKTSTSPIVKSFNRNEC

Anti-idiotypic Anti-PD-L1 Antibody 105D11 Heavy Chain Amino Acid Sequence (SEQ ID NO: 60)
EVQLVETGGGLVKPGGSLKLSCAASGFAFSSYDMSWVRQTPEKRLEW

VAYISSGGGSTYYPDTVKGRFTISRDNAKNTLYLQMSSLKSEDTAMY

YCARLVYYDYDDAMDYWGQGTSVTVSSASTKGPSVYPLAPVCGDTTG

SSVTLGCLVKGYFPEPVTLTWNSGSLSSGVHTFPAVLQSDLYTLSSS

VTVTSSTWPSQSITCNVAHPASSTKVDKKIEPRGPTIKPCPPCKCPA

PNLLGGPSVFIFPPKIKDVLMISLSPIVTCVVVDVSEDDPDVQISWF

VNNVEVHTAQTQTHREDYNSTLRVVSALPIQHQDWMSGKEFKCKVNN

KDLPAPIERTISKPKGSVRAPQVYVLPPPEEEMTKKQVTLTCMVTDF

MPEDIYVEWTNNGKTELNYKNTEPVLDSDGSYFMYSKLRVEKKNWVE

RNSYSCSVVHEGLHNHHTTKSFSRTPGK

Anti-idiotypic Anti-PD-L1 Antibody 43B5 Light Chain Amino Acid Sequence (SEQ ID NO: 61)
DIKMTQSPSSMSVSLGDTVSITCHASQGISSNIGWLQQKPGKSFKGL

IYHGTNLEDGVPSRFSGSGSGADYSLTISSLESEDFADYYCVQYAQF

PLTFGAGTKLELKRADAAPTVSIFPPSSEQLTSGGASVVCFLNNFYP

KDINVKWKIDGSERQNGVLNSWTDQDSKDSTYSMSSTLTLTKDEYER

HNSYTCEATHKTSTSPIVKSFNRNEC

Anti-idiotypic Anti-PD-L1 Antibody 43B5 Heavy Chain Amino Acid Sequence (SEQ ID NO: 62)
EVQLQQSGPELVKPGASVKISCKASGYSFTDYIMLWVKQSHGKSLEW
IGNINPYYGSTSYNLKFKGKATLTVDKSSSTAYMQLNSLTSEDSAVY
YCARWGGNYEGWFAYWGQGTLVTVSAASTKGPSVYPLAPVCGDTTGS
SVTLGCLVKGYFPEPVTLTWNSGSLSSGVHTFPAVLQSDLYTLSSSV
TVTSSTWPSQSITCNVAHPASSTKVDKKIEPRGPTIKPCPPCKCPAP
NLLGGPSVFIFPPKIKDVLMISLSPIVTCVVVDVSEDDPDVQISWFV
NNVEVHTAQTQTHREDYNSTLRVVSALPIQHQDWMSGKEFKCKVNNK
DLPAPIERTISKPKGSVRAPQVYVLPPPEEEMTKKQVTLTCMVTDFM
PEDIYVEWTNNGKTELNYKNTEPVLDSDGSYFMYSKLRVEKKNWVER
NSYSCSVVHEGLHNHHTTKSFSRTPGK

Anti-idiotypic Anti-PD-L1 Antibody 48C1 Light Chain Amino Acid Sequence (SEQ ID NO: 63)
QIVLTQSPAIMSASPGEKVTITCSASSSVSYMHWFQQKPGTSPKLWI
YSTSNLASGVPARFSGSGSGTSYSLTISRMEAEDAATYYCQQRSGYP
PTFGGGTKLEIKRADAAPTVSIFPPSSEQLTSGGASVVCFLNNFYPK
DINVKWKIDGSERQNGVLNSWTDQDSKDSTYSMSSTLTLTKDEYERH
NSYTCEATHKTSTSPIVKSFNRNEC

Anti-idiotypic Anti-PD-L1 Antibody 48C1 Heavy Chain Amino Acid Sequence (SEQ ID NO: 64)
EVQLVESGGGLVKPGGSLKLSCAASGFAFSSYDMSWVRQTPEKRLEW
VAYISSGGGSTYYPDTVKGRFTISRDNAKNTLYLQMSSLKSEDTAMY
YCARTIYYGYDDVMDYWGQGTSVTVSSASTKGPSVYPLAPVCGDTTG
SSVTLGCLVKGYFPEPVTLTWNSGSLSSGVHTFPAVLQSDLYTLSSS
VTVTSSTWPSQSITCNVAHPASSTKVDKKIEPRGPTIKPCPPCKCPA
PNLLGGPSVFIFPPKIKDVLMISLSPIVTCVVVDVSEDDPDVQISWF
VNNVEVHTAQTQTHREDYNSTLRVVSALPIQHQDWMSGKEFKCKVNN
KDLPAPIERTISKPKGSVRAPQVYVLPPPEEEMTKKQVTLTCMVTDF
MPEDIYVEWTNNGKTELNYKNTEPVLDSDGSYFMYSKLRVEKKNWVE
RNSYSCSVVHEGLHNHHTTKSFSRTPGK

---

What is claimed is:

1. An isolated anti-idiotypic antibody that specifically binds to an anti-PD-L1 antibody, wherein the isolated anti-idiotypic antibody comprises a heavy chain variable region comprising HVR-H1, HVR-H2 and HVR-H3 and a light chain variable region comprising HVR-L1, HVR-L2 and HVR-L3, wherein:
   (a) HVR-H1 comprises the amino acid sequence DYIML (SEQ ID NO:43);
   (b) HVR-H2 comprises the amino acid sequence NINPYYGSTSYNLKFKG (SEQ ID NO:44);
   (c) HVR-H3 comprises the amino acid sequence WGG-NYEGWFAY (SEQ ID NO:42);
   (d) HVR-L1 comprises the amino acid sequence HASQ-GISSNIG (SEQ ID NO:20);
   (e) HVR-L2 comprises the amino acid sequence HGTN-LED (SEQ ID NO:21); and
   (f) HVR-L3 comprises the amino acid sequence VQYAQFPLTF (SEQ ID NO:22).

2. The isolated anti-idiotypic antibody of claim 1, wherein the isolated anti-idiotypic antibody comprises a heavy chain variable region comprising the sequence of SEQ ID NO:56 and/or a light chain variable region comprising the sequence of SEQ ID NO:55.

3. An isolated nucleic acid encoding the anti-idiotypic antibody of claim 2.

4. A composition comprising the anti-idiotypic antibody of claim 1.

5. A kit comprising the composition of claim 4.

6. A method for detecting in a biological sample an anti-PD-L1 antibody comprising:
   (a) contacting the biological sample with a capture agent, wherein the capture agent is the composition of claim 4 that binds the anti-PD-L1 antibody present in the sample, thereby forming an immunocomplex;
   (b) contacting the immunocomplex from (a) with a detectable antibody that binds to the anti-PD-L1 antibody; and
   (c) measuring the level of the anti-PD-L1 antibody bound to the anti-idiotypic antibody by detecting the detectable antibody.

7. The method of claim 6, wherein the biological sample is isolated from a human subject.

8. The method of claim 6, wherein the human subject has been treated with an anti-PD-L1 antibody comprising:
   (a) a light chain variable region comprising:
       (i) HVR-L1 comprising the amino acid sequence RASQDVSTAVA (SEQ ID NO:1);
       (ii) HVR-L2 comprising the amino acid sequence SASFLYS (SEQ ID NO:2);
       (iii) HVR-L3 comprising the amino acid sequence QQYLYHPAT (SEQ ID NO:3); and
   (b) a heavy chain variable region comprising:
       (i) HVR-H1 comprising the amino acid sequence GFTFSDSWIH (SEQ ID NO:4);
       (ii) HVR-H2 comprising the amino acid sequence AWISPYGGSTYYADSVKG (SEQ ID NO:5);
       (iii) HVR-H3 comprising the amino acid sequence RHWPGGFDY (SEQ ID NO:6).

9. An immunoassay kit for specifically detecting an anti-PD-L1 antibody in a biological sample, comprising:
   (a) the anti-idiotypic antibody of claim 1;
   (b) a detectable antibody that binds to the anti-PD-L1 antibody; and
   (c) instructions for detecting said anti-PD-L1 antibody.

10. The kit of claim 8, wherein the kit is useful in an immunoassay for detecting the anti-PD-L1 antibody.

11. An isolated anti-idiotypic antibody that specifically binds to an anti-PD-L1 antibody, wherein the isolated anti-idiotypic antibody comprises a heavy chain variable region comprising HVR-H1, HVR-H2 and HVR-H3 and a light chain variable region comprising HVR-L1, HVR-L2 and HVR-L3, wherein:
   (a) HVR-H1 comprises the amino acid sequence SYDMS (SEQ ID NO:51);
   (b) HVR-H2 comprises the amino acid sequence YIS-SGGGSTYYPDTVKG (SEQ ID NO:52);
   (c) HVR-H3 comprises the amino acid sequence TIYYGYDDVMDY (SEQ ID NO:50);
   (d) HVR-L1 comprises the amino acid sequence SASSSVSYMH (SEQ ID NO:26);

(e) HVR-L2 comprises the amino acid sequence STSN-LAS (SEQ ID NO:27); and
(f) HVR-L3 comprises the amino acid sequence QQRSGYPPTF (SEQ ID NO:28).

12. The isolated anti-idiotypic antibody of claim 11, wherein the isolated anti-idiotypic antibody comprises a heavy chain variable region comprising the sequence of SEQ ID NO:58 and/or a light chain variable region comprising the sequence of SEQ ID NO:57.

13. An isolated nucleic acid encoding the anti-idiotypic antibody of claim 12.

14. A composition comprising the anti-idiotypic antibody of claim 11.

15. A kit comprising the composition of claim 14.

16. A method for detecting in a biological sample an anti-PD-L1 antibody comprising:
(a) contacting the biological sample with a capture agent, wherein the capture agent is the composition of claim 14, thereby forming an immunocomplex;
(b) contacting the immunocomplex from (a) with a detectable antibody that binds to the anti-PD-L1 antibody; and
(c) measuring the level of the anti-PD-L1 antibody bound to the composition by detecting the detectable antibody.

17. The method of claim 16, wherein the biological sample is isolated from a human subject.

18. The method of claim 17, wherein the human subject has been treated with an anti-PD-L1 antibody comprising:
(a) a light chain variable region comprising:
 (i) HVR-L1 comprising the amino acid sequence RASQDVSTAVA (SEQ ID NO:1);
 (ii) HVR-L2 comprising the amino acid sequence SASFLYS (SEQ ID NO:2);
 (iii) HVR-L3 comprising the amino acid sequence QQYLYHPAT (SEQ ID NO:3); and
(b) a heavy chain variable region comprising:
 (i) HVR-H1 comprising the amino acid sequence GFTFSDSWIH (SEQ ID NO:4);
 (ii) HVR-H2 comprising the amino acid sequence AWISPYGGSTYYADSVKG (SEQ ID NO:5);
 (iii) HVR-H3 comprising the amino acid sequence RHWPGGFDY (SEQ ID NO:6).

19. An immunoassay kit for specifically detecting an anti-PD-L1 antibody in a biological sample, comprising:
(a) the anti-idiotypic antibody of claim 11;
(b) a detectable antibody that binds to the anti-PD-L1 antibody; and
(c) instructions for detecting said anti-PD-L1 antibody.

20. The kit of claim 19, wherein the kit is useful in an immunoassay for detecting the anti-PD-L1 antibody.

21. A method for detecting an anti-PD-L1 antibody in a biological sample, comprising:
(a) contacting the biological sample with an anti-idiotypic antibody of claim 11 under a condition to allow binding of the anti-idiotypic antibody to the anti-PD-L1 antibody to form a complex;
(b) analyzing the sample by Immunofixation Electrophoresis to compare the sample contacted with the anti-idiotypic antibody to the sample that has not been contacted with the anti-idiotypic antibody;
(c) detecting the presence of the anti-PD-L1 antibody in the biological sample; wherein a difference in the migration between the sample contacted with the anti-idiotypic antibody and the sample that has not been contacted with the anti-idiotypic antibody indicates the presence of the anti-PD-L1 antibody in the biological sample.

22. An isolated nucleic acid encoding an anti-idiotypic antibody that specifically binds to an anti-PD-L1 antibody, wherein the anti-idiotypic antibody comprises a heavy chain variable region comprising HVR-H1, HVR-H2 and HVR-H3 and a light chain variable region comprising HVR-L1, HVR-L2 and HVR-L3, wherein:
(a) HVR-H1 comprises the amino acid sequence DYIML (SEQ ID NO:43);
(b) HVR-H2 comprises the amino acid sequence NINPYYGSTSYNLKFKG (SEQ ID NO:44);
(c) HVR-H3 comprises the amino acid sequence WGG-NYEGWFAY (SEQ ID NO:42);
(d) HVR-L1 comprises the amino acid sequence HASQ-GISSNIG (SEQ ID NO:20);
(e) HVR-L2 comprises the amino acid sequence HGTN-LED (SEQ ID NO:21); and
(f) HVR-L3 comprises the amino acid sequence VQYAQFPLTF (SEQ ID NO:22).

23. A vector comprising the nucleic acid of claim 22.

24. A host cell comprising the vector of claim 23.

25. A process for making an anti-idiotypic antibody comprising culturing the host cell of claim 24 under conditions suitable for the expression of the vector encoding the anti-idiotypic antibody and recovering the anti-idiotypic antibody.

26. An isolated nucleic acid encoding an anti-idiotypic antibody that specifically binds to an anti-PD-L1 antibody, wherein the anti-idiotypic antibody comprises a heavy chain variable region comprising HVR-H1, HVR-H2 and HVR-H3 and a light chain variable region comprising HVR-L1, HVR-L2 and HVR-L3, wherein:
(a) HVR-H1 comprises the amino acid sequence SYDMS (SEQ ID NO:51);
(b) HVR-H2 comprises the amino acid sequence YIS-SGGGSTYYPDTVKG (SEQ ID NO:52);
(c) HVR-H3 comprises the amino acid sequence TIYYGYDDVMDY (SEQ ID NO:50);
(d) HVR-L1 comprises the amino acid sequence SASSSVSYMH (SEQ ID NO:26);
(e) HVR-L2 comprises the amino acid sequence STSN-LAS (SEQ ID NO:27); and
(f) HVR-L3 comprises the amino acid sequence QQRSGYPPTF (SEQ ID NO:28).

27. A vector comprising the nucleic acid of claim 26.

28. A host cell comprising the vector of claim 27.

29. A process for making an anti-idiotypic antibody comprising culturing the host cell of claim 28 under conditions suitable for the expression of the vector encoding the anti-idiotypic antibody and recovering the anti-idiotypic antibody.

* * * * *

UNITED STATES PATENT AND TRADEMARK OFFICE
CERTIFICATE OF CORRECTION

| | |
|---|---|
| PATENT NO. | : 11,279,762 B2 |
| APPLICATION NO. | : 16/511323 |
| DATED | : March 22, 2022 |
| INVENTOR(S) | : Jo-Anne Hongo |

It is certified that error appears in the above-identified patent and that said Letters Patent is hereby corrected as shown below:

In the Claims

At Column 90, Claim number 10, Line number 51, please delete "claim 8" and replace with --claim 9--.

Signed and Sealed this
Fourteenth Day of June, 2022

Katherine Kelly Vidal
*Director of the United States Patent and Trademark Office*

SEQUENCE LISTING

```
<160> NUMBER OF SEQ ID NOS: 64

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Arg Ala Ser Gln Asp Val Ser Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3
```

```
Gln Gln Tyr Leu Tyr His Pro Ala Thr
1               5
```

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

```
Gly Phe Thr Phe Ser Asp Ser Trp Ile His
1               5                   10
```

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

```
Ala Trp Ile Ser Pro Tyr Gly Gly Ser Thr Tyr Tyr Ala Asp Ser Val
1               5                   10                  15

Lys Gly
```

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

```
Arg His Trp Pro Gly Gly Phe Asp Tyr
1               5
```

<210> SEQ ID NO 7
<211> LENGTH: 108
<212> TYPE: PRT
<213> ORGANISM: Artificial Sequence
<220> FEATURE:
<223> OTHER INFORMATION: Synthetic Construct

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105
```

<210> SEQ ID NO 8
<211> LENGTH: 122
<212> TYPE: PRT

<213> ORGANISM: Artificial Sequence
<220> FEATURE:
<223> OTHER INFORMATION: Synthetic Construct

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120
```

<210> SEQ ID NO 9
<211> LENGTH: 214
<212> TYPE: PRT
<213> ORGANISM: Artificial Sequence
<220> FEATURE:
<223> OTHER INFORMATION: Synthetic Construct

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 10
<211> LENGTH: 447
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Val Ser Tyr Met His Trp Phe
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Leu Trp Ile Tyr Ser Thr Ser Asn Leu Ala
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gln Gln Arg Ser Ser Tyr Pro Pro Thr
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Ser Ala Ser Ser Ser Val Ser Tyr Met His
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15
```

Ser Thr Ser Asn Leu Ala Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gln Gln Arg Ser Ser Tyr Pro Pro Thr Phe
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Ser Ser Asn Ile Gly Trp Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Gly Leu Ile Tyr His Gly Thr Asn Leu Glu
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Val Gln Tyr Ala Gln Phe Pro Leu Thr
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

His Ala Ser Gln Gly Ile Ser Ser Asn Ile Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

His Gly Thr Asn Leu Glu Asp
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Val Gln Tyr Ala Gln Phe Pro Leu Thr Phe
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Val Ser Tyr Met His Trp Phe
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Leu Trp Ile Tyr Ser Thr Ser Asn Leu Ala
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Gln Gln Arg Ser Gly Tyr Pro Pro Thr
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Ser Ala Ser Ser Ser Val Ser Tyr Met His
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Ser Thr Ser Asn Leu Ala Ser

```
<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gln Gln Arg Ser Gly Tyr Pro Pro Thr Phe
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Ser Ser Tyr Asp Met Ser
1               5

<210> SEQ ID NO 30
<211> LENGTH: 13
<212> TYPE: PRT
<213> ORGANISM: Artificial Sequence
<220> FEATURE:
<223> OTHER INFORMATION: Synthetic Construct

<400> SEQUENCE: 30

Trp Val Ala Tyr Ile Ser Ser Gly Gly Gly Ser Thr Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Ala Arg Leu Val Tyr Tyr Asp Tyr Asp Asp Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Gly Phe Ala Phe Ser Ser Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Ser Ser Gly Gly Gly Ser
1               5
```

```
<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Leu Val Tyr Tyr Asp Tyr Asp Asp Ala Met Asp Tyr
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Ser Tyr Asp Met Ser
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Tyr Ile Ser Ser Gly Gly Gly Ser Thr Tyr Tyr Pro Asp Thr Val Lys
1               5                   10                  15

Gly

<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Thr Asp Tyr Ile Met Leu
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetic Construct

<400> SEQUENCE: 38

Trp Ile Gly Asn Ile Asn Pro Tyr Tyr Gly Ser Thr Ser
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Ala Arg Trp Gly Gly Asn Tyr Glu Gly Trp Phe
```

```
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Gly Tyr Ser Phe Thr Asp Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Asn Pro Tyr Tyr Gly Ser
1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Trp Gly Gly Asn Tyr Glu Gly Trp Phe Ala Tyr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Asp Tyr Ile Met Leu
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Asn Ile Asn Pro Tyr Tyr Gly Ser Thr Ser Tyr Asn Leu Lys Phe Lys
1               5                   10                  15

Gly

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45
```

Ser Ser Tyr Asp Met Ser
1               5

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Trp Val Ala Tyr Ile Ser Ser Gly Gly Gly Ser Thr Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Ala Arg Thr Ile Tyr Tyr Gly Tyr Asp Asp Val
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Gly Phe Ala Phe Ser Ser Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct

<400> SEQUENCE: 49

Ser Ser Gly Gly Gly Ser
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Thr Ile Tyr Tyr Gly Tyr Asp Asp Val Met Asp Tyr
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Synthetic Construct

<400> SEQUENCE: 51

Ser Tyr Asp Met Ser

```
<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

Tyr Ile Ser Ser Gly Gly Gly Ser Thr Tyr Tyr Pro Asp Thr Val Lys
1               5                   10                  15
Gly

<210> SEQ ID NO 53
<211> LENGTH: 106
<212> TYPE: PRT
<213> ORGANISM: Artificial Sequence
<220> FEATURE:
<223> OTHER INFORMATION: Synthetic Construct

<400> SEQUENCE: 53

Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Arg Leu Glu Ile Lys
            100                 105

<210> SEQ ID NO 54
<211> LENGTH: 121
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Thr Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Val Tyr Tyr Asp Tyr Asp Asp Ala Met Asp Tyr Trp Gly
            100                 105                 110
```

Gln Gly Thr Ser Val Thr Val Ser Ser
        115                 120

<210> SEQ ID NO 55
<211> LENGTH: 107
<212> TYPE: PRT
<213> ORGANISM: Artificial Sequence
<220> FEATURE:
<223> OTHER INFORMATION: Synthetic Construct

<400> SEQUENCE: 55

Asp Ile Lys Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Leu
                85                  90                  95

Thr Phe Gly Ala Gly Thr Lys Leu Glu Leu Lys
            100                 105

<210> SEQ ID NO 56
<211> LENGTH: 120
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Tyr Gly Ser Thr Ser Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Gly Gly Asn Tyr Glu Gly Trp Phe Ala Tyr Trp Gly Gln
            100                 105                 110

Gly Thr Leu Val Thr Val Ser Ala
        115                 120

<210> SEQ ID NO 57
<211> LENGTH: 106
<212> TYPE: PRT
<213> ORGANISM: Artificial Sequence
<220> FEATURE:
<223> OTHER INFORMATION: Synthetic Construct

<400> SEQUENCE: 57

Gln Ile Val Leu Thr Gln Ser Pro Ala Ile Met Ser Ala Ser Pro Gly

```
              1               5                  10                 15
            Glu Lys Val Thr Ile Thr Cys Ser Ala Ser Ser Ser Val Ser Tyr Met
                           20                  25                 30

His Trp Phe Gln Gln Lys Pro Gly Thr Ser Pro Lys Leu Trp Ile Tyr
                           35                  40                 45

Ser Thr Ser Asn Leu Ala Ser Gly Val Pro Ala Arg Phe Ser Gly Ser
                           50                  55                 60

Gly Ser Gly Thr Ser Tyr Ser Leu Thr Ile Ser Arg Met Glu Ala Glu
             65                70                 75                 80

Asp Ala Ala Thr Tyr Tyr Cys Gln Gln Arg Ser Gly Tyr Pro Pro Thr
                           85                  90                 95

Phe Gly Gly Gly Thr Lys Leu Glu Ile Lys
                          100                105
```

<210> SEQ ID NO 58
<211> LENGTH: 121
<212> TYPE: PRT
<213> ORGANISM: Artificial Sequence
<220> FEATURE:
<223> OTHER INFORMATION: Synthetic Construct

<400> SEQUENCE: 58

```
            Glu Val Gln Leu Val Glu Ser Gly Gly Gly Leu Val Lys Pro Gly Gly
             1               5                  10                 15

Ser Leu Lys Leu Ser Cys Ala Ala Ser Gly Phe Ala Phe Ser Ser Tyr
                           20                  25                 30

Asp Met Ser Trp Val Arg Gln Thr Pro Glu Lys Arg Leu Glu Trp Val
                           35                  40                 45

Ala Tyr Ile Ser Ser Gly Gly Gly Ser Thr Tyr Tyr Pro Asp Thr Val
                           50                  55                 60

Lys Gly Arg Phe Thr Ile Ser Arg Asp Asn Ala Lys Asn Thr Leu Tyr
             65                70                 75                 80

Leu Gln Met Ser Ser Leu Lys Ser Glu Asp Thr Ala Met Tyr Tyr Cys
                           85                  90                 95

Ala Arg Thr Ile Tyr Tyr Gly Tyr Asp Asp Val Met Asp Tyr Trp Gly
                          100                 105                110

Gln Gly Thr Ser Val Thr Val Ser Ser
                          115                120
```

<210> SEQ ID NO 59
<211> LENGTH: 213
<212> TYPE: PRT
<213> ORGANISM: Artificial Sequence
<220> FEATURE:
<223> OTHER INFORMATION: Synthetic Construct

<400> SEQUENCE: 59

```
            Asp Ile Val Leu Thr Gln Ser Pro Ala Ile Met Ser Ala Ser Pro Gly
             1               5                  10                 15

Glu Lys Val Thr Ile Thr Cys Ser Ala Ser Ser Ser Val Ser Tyr Met
                           20                  25                 30

His Trp Phe Gln Gln Lys Pro Gly Thr Ser Pro Lys Leu Trp Ile Tyr
                           35                  40                 45

Ser Thr Ser Asn Leu Ala Ser Gly Val Pro Ala Arg Phe Ser Gly Ser
                           50                  55                 60

Gly Ser Gly Thr Ser Tyr Ser Leu Thr Ile Ser Arg Met Glu Ala Glu
             65                70                 75                 80
```

```
Asp Ala Ala Thr Tyr Tyr Cys Gln Gln Arg Ser Ser Tyr Pro Pro Thr
                85                  90                  95

Phe Gly Gly Gly Thr Arg Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
210

<210> SEQ ID NO 60
<211> LENGTH: 451
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Thr Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ser Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Val Tyr Tyr Asp Tyr Asp Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Tyr Pro Leu Ala Pro Val Cys Gly Asp Thr Thr Gly Ser Ser Val
130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
210                 215                 220
```

```
Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
            245                 250                 255

Ile Ser Leu Ser Pro Ile Val Thr Cys Val Val Val Asp Val Ser Glu
        260                 265                 270

Asp Asp Pro Asp Val Gln Ile Ser Trp Phe Val Asn Asn Val Glu Val
    275                 280                 285

His Thr Ala Gln Thr Gln Thr His Arg Glu Asp Tyr Asn Ser Thr Leu
290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly Lys
        450

<210> SEQ ID NO 61
<211> LENGTH: 214
<212> TYPE: PRT
<213> ORGANISM: Artificial Sequence
<220> FEATURE:
<223> OTHER INFORMATION: Synthetic Construct

<400> SEQUENCE: 61

Asp Ile Lys Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125
```

```
Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 62
<211> LENGTH: 450
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Tyr Gly Ser Thr Ser Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Gly Gly Asn Tyr Glu Gly Trp Phe Ala Tyr Trp Gly Gln
            100                 105                 110

Gly Thr Leu Val Thr Val Ser Ala Ala Ser Thr Lys Gly Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270
```

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 63
<211> LENGTH: 213
<212> TYPE: PRT
<213> ORGANISM: Artificial Sequence
<220> FEATURE:
<223> OTHER INFORMATION: Synthetic Construct

<400> SEQUENCE: 63

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Gly Tyr Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

```
Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 64
<211> LENGTH: 451
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg Thr Ile Tyr Tyr Gly Tyr Asp Asp Val Met Asp Tyr Trp Gly
            100                 105                 110

Gln Gly Thr Ser Val Thr Val Ser Ser Ala Ser Thr Lys Gly Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320
```

```
Lys Glu Phe Lys Cys Lys Val Asn Asn Lys Asp Leu Pro Ala Pro Ile
                325             330             335

Glu Arg Thr Ile Ser Lys Pro Lys Gly Ser Val Arg Ala Pro Gln Val
            340             345             350

Tyr Val Leu Pro Pro Glu Glu Glu Met Thr Lys Lys Gln Val Thr
        355             360             365

Leu Thr Cys Met Val Thr Asp Phe Met Pro Glu Asp Ile Tyr Val Glu
    370             375             380

Trp Thr Asn Asn Gly Lys Thr Glu Leu Asn Tyr Lys Asn Thr Glu Pro
385             390             395             400

Val Leu Asp Ser Asp Gly Ser Tyr Phe Met Tyr Ser Lys Leu Arg Val
            405             410             415

Glu Lys Lys Asn Trp Val Glu Arg Asn Ser Tyr Ser Cys Ser Val Val
            420             425             430

His Glu Gly Leu His Asn His His Thr Thr Lys Ser Phe Ser Arg Thr
            435             440             445

Pro Gly Lys
    450
```